US011331415B2

(12) United States Patent
Oldinski et al.

(10) Patent No.: US 11,331,415 B2
(45) Date of Patent: May 17, 2022

(54) SUPRAMOLECULAR ALGINATE MATERIALS FOR BIOMEDICAL APPLICATIONS

(71) Applicant: University of Vermont and State Agricultural College, Burlington, VT (US)

(72) Inventors: Rachael A. Oldinski, Burlington, VT (US); Jennifer N. Etter, Essex Junction, VT (US)

(73) Assignee: UNIVERSITY OF VERMONT AND STATE AGRICULTURAL COLLEGE, Burlington, VT (US)

( * ) Notice: Subject to any disclaimer, the term of this patent is extended or adjusted under 35 U.S.C. 154(b) by 0 days.

(21) Appl. No.: 16/381,718

(22) Filed: Apr. 11, 2019

(65) Prior Publication Data
US 2019/0314555 A1 Oct. 17, 2019

Related U.S. Application Data

(60) Provisional application No. 62/656,186, filed on Apr. 11, 2018.

(51) Int. Cl.
| | |
|---|---|
| *A61L 27/52* | (2006.01) |
| *A61K 9/06* | (2006.01) |
| *A61L 27/20* | (2006.01) |
| *A61K 9/51* | (2006.01) |
| *A61L 31/16* | (2006.01) |
| *A61K 47/36* | (2006.01) |

(52) U.S. Cl.
CPC ............... *A61L 27/52* (2013.01); *A61K 9/06* (2013.01); *A61K 9/5153* (2013.01); *A61L 27/20* (2013.01); *A61K 47/36* (2013.01); *A61L 31/16* (2013.01); *A61L 2300/64* (2013.01)

(58) Field of Classification Search
CPC ......... A61K 47/36; A61K 9/5153; C08L 5/04; C08L 5/10
See application file for complete search history.

(56) References Cited

U.S. PATENT DOCUMENTS

2015/0202299 A1* 7/2015 Burdick ................ A61L 31/145
424/85.2

OTHER PUBLICATIONS

Hunt et al. (Acta Biomaterialia, Feb. 2017, vol. 49, pp. 329-343) (Year: 2017).*
Tan et al. (Soft Matter, 2012, vol. 8, pp. 5746-5749) (Year: 2012).*
Jeon et al. (Journal of Controlled Release, 2011, vol. 154, pp. 258-266) (Year: 2011).*
Sun et al (Materials, 2013, vol. 6, pp. 1285-1309) (Year: 2013).*
Jeon, et al.,"Affinity-based growth factor delivery using biodegradable, photocrosslinked heparin-alginate hydrogels." J Control Release. Sep. 25, 2011; 154(3): 258-266.

* cited by examiner

*Primary Examiner* — Mark V Stevens
(74) *Attorney, Agent, or Firm* — Saul Ewing Arnstein & Lehr LLP; Kathryn Doyle

(57) ABSTRACT

The present invention relates to the unexpected discovery of novel hydrogel formulations that allow for the encapsulation and delivery of living cells and/or drugs to a subject in need thereof. In certain embodiments, the hydrogel compositions of the invention comprise bound bioactive molecules that promote long-term cell viability and allows for the development of vasculature. The invention further provides methods of delivering viable cells and/or drugs to a subject comprising administering the compositions of the invention to the subject in need thereof.

35 Claims, 7 Drawing Sheets

FIG. 1A
FIG. 1B
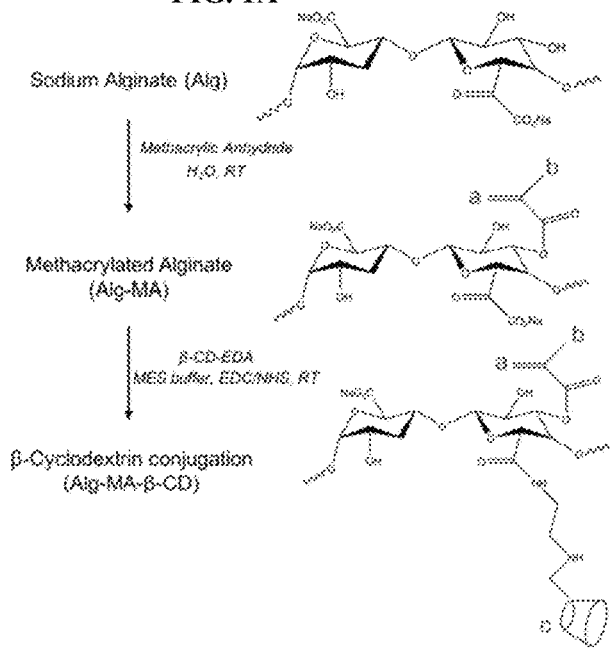
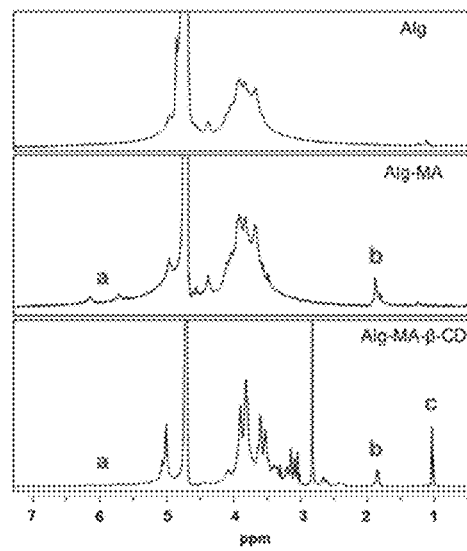
FIGs. 2A-2D
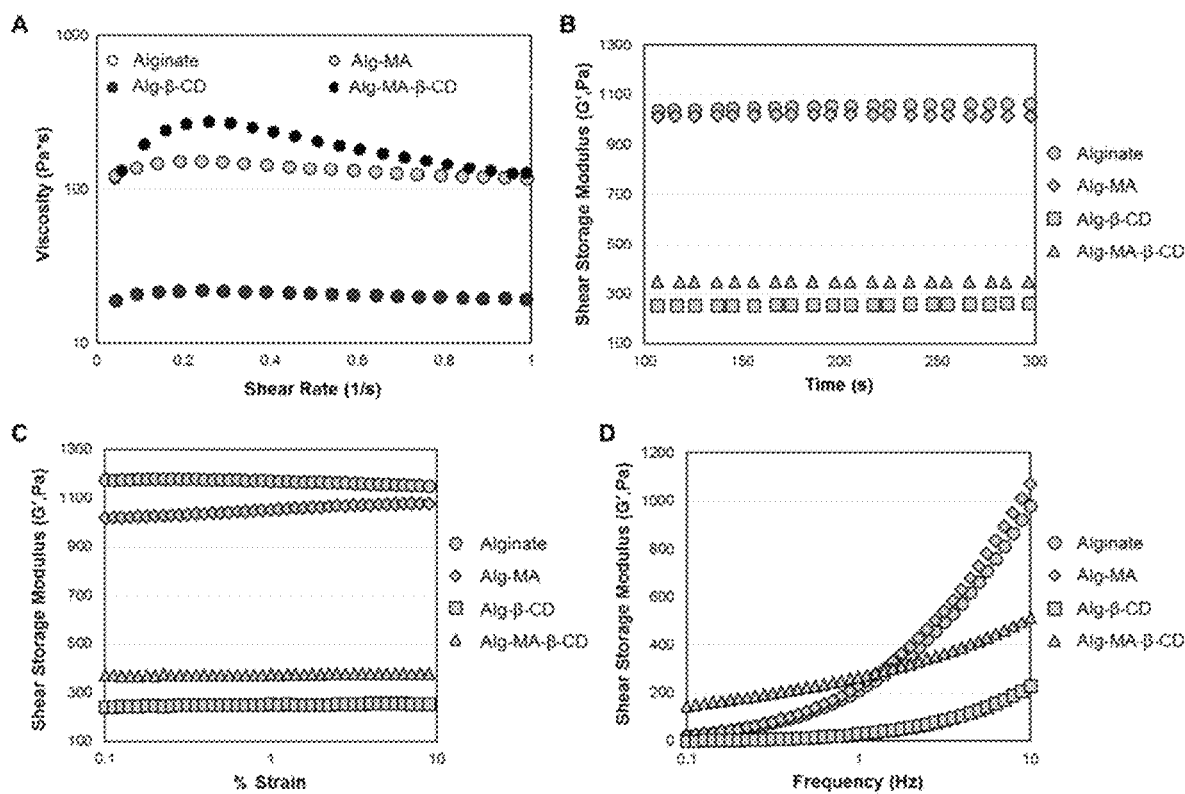

SUPRAMOLECULAR ALGINATE MATERIALS FOR BIOMEDICAL APPLICATIONS

CROSS-REFERENCE TO RELATED APPLICATIONS

This application claims the benefit of priority under 35 U.S.C. § 119(e) to U.S. Provisional Patent Application No. 62/656,186, filed Apr. 11, 2018, the contents of which are incorporated by reference herein in their entirety.

STATEMENT REGARDING FEDERALLY SPONSORED RESEARCH OR DEVELOPMENT

This invention was made with government support under grant number EB020964 awarded by the National Institutes of Health (NIH). The government has certain rights in the invention.

BACKGROUND OF THE INVENTION

Although the field of tissue engineering has been successful in engineering simple tissues, a number of challenges remain in engineering or regenerating complex, hybrid tissues. Thus, cell therapy is an attractive option which aids the body in wound healing and tissue regeneration. Cell and drug encapsulation and delivery within hydrogels is an attractive method for treating, healing and restoring a variety of tissues and treating a variety of diseases and disorders. Hence, there is an increasing need to develop biomaterial platforms to deliver and maintain viable cells or bioactive compounds, and to treat a disease, heal a wound, and/or restore natural tissue function.

There remains a need in the art for materials and methods for delivering cells and/or drugs to a patient in need thereof. In certain embodiments, these materials and methods can include hydrogels, and uses thereof, which incorporate a number of functionalities which controllably alter one or more properties such as cell adhesion, tissue adhesion, cell differentiation, cell viability, and neovascularization. In certain embodiments, the materials should mimic the mechanical properties of natural tissue. The present invention addresses these needs.

SUMMARY OF THE INVENTION

The present invention provides a hydrogel composition having at least one selected from alginate (Alg) and methacrylated alginate (Alg-MA); β-cyclodextrin (β-CD); and at least one additional component selected from the group consisting of heparin (hep) and arginylglycylaspartic acid (RGD); wherein the β-cyclodextrin (β-CD) and the at least one additional component are each covalently bound to the alginate or methacrylated alginate. In certain embodiments, the hydrogel further includes at least one crosslinking component selected from the group consisting of polypropylene glycol (PPG), polyethylene glycol (PEG), polyethylene oxide (PEO), PEG-b-PPG-b-PEG copolymers, PEO-b-PPG-b-PEO copolymers, agarose, amylase, amylpectin, cellularose, chitosan, collagen, fibrin, gelatin, glycogenhyaluronic acid, poly(acrylamide), poly(β-aminoester), poly(caprolactone), matrigel, multi-arm polyethylene glycol, poly-hydroxyethyl acrylate, poly(hydroxyethyl methacrylate), poly (N-isopropylacrylamide), poly(glycolic acid), poly(lactic acid), poly(lactic acid-glycolic acid), oligo(poly(ethylene glycol)fumarate), poly(vinyl alcohol), poly(vinyl acid), 1-ethyl-3-[3-dimethylaminopropyl] carbodiimide hydrochloride (EDC), and N-hydroxysuccinimide (NHS). In some embodiments, the alginate and β-cyclodextrin forms a supramolecular complex with the at least one crosslinking component.

In certain embodiments, the hydrogel further includes living cells. In some embodiments, the living cells are encapsulated within the hydrogel composition. In some embodiments, the living cells are eukaryotic cells. In some embodiments, the living cells are progenitor cells. In some embodiments, the living cells are human mesenchymal stem cells.

In certain embodiments, the hydrogel further includes at least one pharmaceutically active compound. In some embodiments, the at least one pharmaceutically active compound is encapsulated within the hydrogel composition. In some embodiments, the at least one pharmaceutically active compound is non-covalently bound to the hydrogel composition through a guest-host interaction with the a β-cyclodextrin moiety.

In certain embodiments, the hydrogel further includes at least one biological factor. In some embodiments the at least one biological factor modifies one or more cellular functions selected from the group consisting of cell growth, cell viability, cell adhesion, tissue adhesion, and progenitor cell differentiation. In some embodiments, the at least one biological factor is a heparin or RGD binding protein. In some embodiments, the at least one biological factor is selected from the group consisting of epidermal growth factor (EGF), platelet derived growth factor (PDGF), basic fibroblast growth factor (bFGF), transforming growth factor-beta (TGF-β), and tissue inhibitors of metalloproteinases (TIMP). In some embodiments, the at least one biological factor is non-covalently bound to the hydrogel composition through a guest-host interaction with the a β-cyclodextrin moiety.

In certain embodiments, the hydrogel composition is in the form of a microsphere composition. In some embodiments, the microsphere composition comprises monodisperse microspheres. In some embodiments, the microsphere composition comprises microspheres having a diameter of about 500 nm to about 80 μm. In some embodiments, the hydrogel composition is formulated as part of a pharmaceutical composition. In some embodiments, the pharmaceutical composition further comprises at least one pharmaceutically acceptable carrier. In some embodiments, the pharmaceutical composition is in a form selected from the group consisting of a cream, liquid, gel, spray, ointment, 3-D scaffold, powder, patch and graft.

In certain aspects the present invention further relates to a method of delivering viable living cells to a subject, the method comprising administering to the subject a hydrogel composition comprising alginate, β-cyclodextrin, living cells and at least one additional component selected from the group consisting of heparin and RGD wherein the at least one additional component is covalently bound to the alginate and wherein the alginate is optionally methacrylated. In some embodiments, the living cells are encapsulated within the hydrogel composition. In some embodiments, the living cells are eukaryotic cells. In some embodiments, the living cells are progenitor cells. In some embodiments, the living cells are human mesenchymal stem cells. In some embodiments, the method treats at least one disease or disorder in the subject selected from the group consisting of immune-mediated diseases, skeletal tissue injury, of immune-mediated diseases, skeletal/cranial tissue injury, skeletal diseases, skin wounds, internal organ wounds, cancers, inflammatory diseases, infections, and chronic wounds.

In certain aspects the present invention provides a method of treating a wound in a subject in need thereof, the method comprising contacting the wound with a hydrogel composition comprising alginate, β-cyclodextrin modified alginate, living cells and at least one additional component selected from the group consisting of heparin and RGD wherein the at least one additional component is covalently bound to the alginate and wherein the alginate is optionally methacrylated. In some embodiments, the living cells are encapsulated within the hydrogel composition. In some embodiments, the living cells are eukaryotic cells. In some embodiments, the living cells are progenitor cells. In some embodiments, the living cells are human mesenchymal stem cells. In some embodiments, the hydrogel composition is in the form of cream, liquid, gel, spray, ointment, 3-D scaffold, powder, patch or graft. In some embodiments, the hydrogel composition is disposed on the surface of a bandage, patch, secondary hydrogel scaffold or graft.

BRIEF DESCRIPTION OF THE DRAWINGS

The following detailed description of specific embodiments of the invention will be better understood when read in conjunction with the appended drawings. For the purpose of illustrating the invention, there are shown in the drawings specific embodiments. It should be understood, however, that the invention is not limited to the precise arrangements and instrumentalities of the embodiments shown in the drawings.

FIGS. 1A-1B depict the chemical synthesis and characterization of stimuli-responsive alginate materials according to an exemplary embodiment of the invention, via sequential aqueous-based methacrylation and β-CD conjugation reactions. FIG. 1A shows the chemical structures of non-modified sodium alginate (Alg, top), methacrylated alginate (Alg-MA, middle), and methacrylated alginate conjugated with β-cyclodextrin (Alg-MA-β-CD, bottom). FIG. 1B is an $^1$H-NMR spectral analysis of sodium alginate (top), methacrylated alginate (middle), and methacrylated alginate conjugated with β-CD (bottom). Peaks 'a' and 'b' demonstrate methacrylation of the alginate, and peak 'c' shows the conjugation of the β-CD onto Alg-MA.

FIGS. 2A-2D are graphs showing rheological data for alginate controls (Alg), and chemically modified alginate (Alg-MA, Alg-β-CD, Alg-MA-β-CD), measured at 25° C. to characterize the material properties. FIG. 2A is a graph of viscosity (Pa*s) values determined at increasing radial shear rates. FIG. 2B is a graph of oscillatory time sweeps performed at 1% radial strain, 10 Hz, and the loss (G") and storage (G') shear moduli for Alg controls and chemically modified alginate were calculated. G' values were also calculated at increasing shear strains at 1 Hz (FIG. 2C), and increasing frequencies at 0.5% radial strain (FIG. 2D).

(FIG. 3A) Increasing temperatures, at 1% radial strain and 1 Hz, to examine the effects of β-CD conjugation, and Pluronic® F-108 addition (1:1 weight ratio). FIG. 3A shows the effect of temperature on hydrogel pre-cursor solutions containing the thermo-responsive polymer Pluroinc F-108. FIG. 3B shows the effect of green light exposure on various chemically-modified alginates. Exposure to green light, starting 1 minute into the experiment, for 10 minutes at 1% radial strain, 1 Hz, and 37° C.

As shown in FIG. 4A, shear storage (G') moduli were calculated after performing the following rheological method: 1) Increasing temperature from 25° C. to 37° C., at 1% radial strain and 1 Hz, to examine the effects of β-CD conjugation, and Pluronic® F-127 addition (1:1 weight ratio); 2) exposure to green light, after 1 minute of equilibration at 37° C., for 10 minutes at 1% radial strain, 1 Hz, and 37° C., to examine the effect of covalent crosslinking on modified alginate materials; and 3) addition of 100 mM calcium chloride ($CaCl_2$) solution to examine the effects of ionic crosslinking on the modified alginate materials (after increasing temperature and covalent crosslinking). FIG. 4B reports quantitative G' values for the non-modified alginate controls, and chemically-modified alginate hydrogels, showing the effect of three different and sequential crosslinking techniques (mean±standard deviation, n=3).

As shown in FIG. 5A, shear storage (G') moduli were calculated after performing the following rheological methods: 1) Increasing temperature from 25° C. to 37° C., at 1% radial strain and 1 Hz, to examine the effects of β-CD conjugation, and Pluronic® addition (1:1 weight ratio); 2) exposure to green light, after 1 minute of equilibration at 37° C., for 10 minutes at 1% radial strain, 1 Hz, and 37° C., to examine the effect of covalent crosslinking on modified alginate materials; and 3) addition of 100 mM calcium chloride ($CaCl_2$) solution to examine the effects of ionic crosslinking on the modified alginate materials (after increasing temperature and covalent crosslinking). FIG. 5B reports the quantitative G' values for various Alg-MA-β-CD:Pluronic® hydrogels, showing the effect of three different and sequential crosslinking techniques, the effect of polymer concentration, and the effect of Pluronic® copolymer selection (mean±standard deviation, n=3).

FIG. 8B shows living cells, while FIG. 8C shows dead cells.

DETAILED DESCRIPTION OF THE INVENTION

Figure 3A:
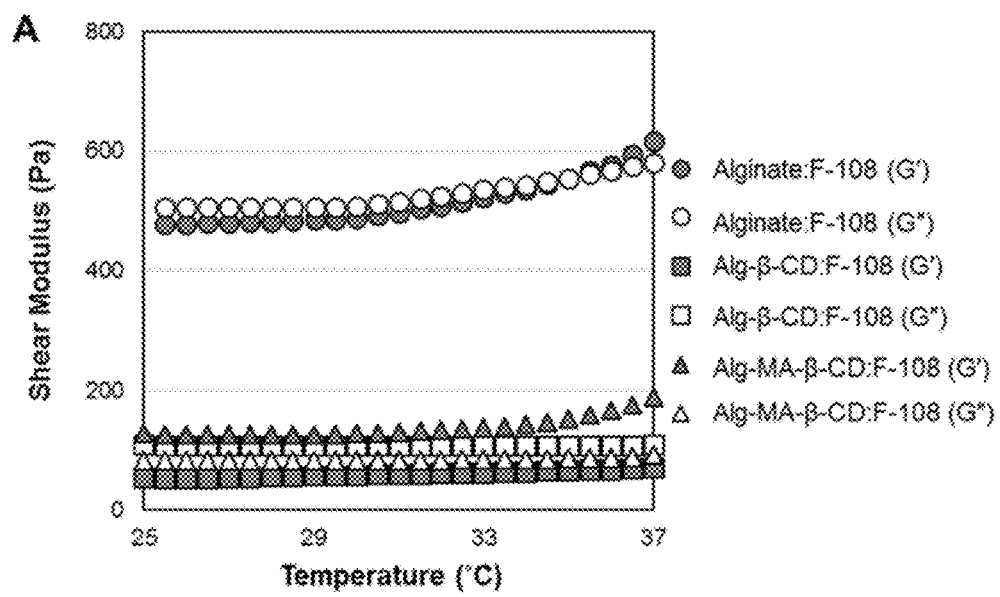
FIGS. 3A-3B are graphs showing gelation kinetics for alginate controls (Alg) and chemically modified alginate (Alg-MA, Alg-β-CD, Alg-MA-β-CD) hydrogels. Shear loss (G") and storage (G') moduli were collected using the following rheological methods.

In one aspect, the present invention relates to the unexpected discovery of novel hydrogel formulations that allow for the encapsulation and delivery of living cells to a subject in need thereof. In certain embodiments, the hydrogel compositions of the invention comprise bound bioactive molecules that promote long-term cell viability and allows for the development of vasculature in developing tissue. In another aspect, the invention relates to methods of delivering viable cells and/or drugs to a subject comprising administering the compositions of the invention to the subject in need thereof.

Definitions

As used herein, each of the following terms has the meaning associated with it in this section.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, exemplary methods and materials are described.

Generally, the nomenclature used herein and the laboratory procedures in tissue engineering and biomaterial science are those well-known and commonly employed in the art.

As used herein, the articles "a" and "an" refer to one or to more than one (i.e., to at least one) of the grammatical object of the article. By way of example, "an element" means one element or more than one element.

As used herein, the term "about" is understood by persons of ordinary skill in the art and varies to some extent on the context in which it is used. As used herein when referring to a measurable value such as an amount, a temporal duration, and the like, the term "about" is meant to encompass variations of ±20% or ±10%, more preferably ±5%, even more preferably ±1%, and still more preferably ±0.1% from the specified value, as such variations are appropriate to perform the disclosed methods.

As used herein, the term "composition" or "pharmaceutical composition" refers to a mixture of at least one compound useful within the invention with a pharmaceutically acceptable carrier. The pharmaceutical composition facilitates administration of the compound to a patient or subject. Multiple techniques of administering a compound exist in the art including, but not limited to, intravenous, injection, oral, aerosol, parenteral, ophthalmic, nasal, pulmonary and topical administration.

As used herein, the terms "covalently bound" or "covalently conjugated" refers to the formation of a covalent bond between two chemical species or moieties. Covalent bonds are to be taken to have the meaning commonly accepted in the art, referring to a chemical bond that involves the sharing of electron pairs between atoms.

As used herein "crosslinking" is meant to be a process of creating a bond that links one polymer chain to another. Crosslinking bonds are often in the form of covalent bonds or ionic bonds, however in some instances crosslinking can take place through non-covalent interactions, such as but not limited to hydrogen bonds, pi stacking interactions or metal-ligand coordination.

As used herein "crosslinking agent" or "crosslinking source" is meant to be an agent that is capable of forming a chemical or ionic link between molecules. Nonlimiting examples of crosslinking agents or sources include divalent metal cations (i.e., calcium chloride); ammonium persulfate (APS) and tetramethylethylenediamine (TEMED), glutaraldehyde, epoxides, oxidized dextran, p-azido benzoylhydrazide, N-[α-maleimidoacetoxy]succinimide ester, p-azidophenyl glyoxal monohydrate, bis-[β-(4-azidosalicylamido) ethyl]disulfide, bis[sulfosuccinimidyl]suberate, dithiobis [succinimidyl proprionate, disuccinimidyl suberate, 1-ethyl-3-[3-dimethylaminopropyl] carbodiimide hydrochloride (EDC), N-hydroxysuccinimide (NHS), eosin Y, triethanolamine, 1-vinyl-2-pyrrolidinone, visible light irradiation, ultraviolet irradiation, and combinations thereof.

A "disease" as used herein is a state of health of an animal wherein the animal cannot maintain homeostasis, and wherein if the disease is not ameliorated then the animal's health continues to deteriorate. In one non-limiting embodiment, a disease can be a cancer.

A "disorder" as used herein in an animal is a state of health in which the animal is able to maintain homeostasis, but in which the animal's state of health is less favorable than it would be in the absence of the disorder. Left untreated, a disorder does not necessarily cause a further decrease in the animal's state of health.

As used herein, the term "gel" refers to a three-dimensional polymeric structure that itself is insoluble in a particular liquid but which is capable of absorbing and retaining large quantities of the liquid to form an air stable, often soft and pliable, but always to one degree or another shape-retentive, structure. When the liquid is water, the gel is referred to as a hydrogel. Unless expressly stated otherwise, the term "gel" will be used throughout this application to refer both to polymeric structures that have absorbed a liquid other than water and to polymeric structures that have absorbed water, it being readily apparent to those skilled in the art from the context whether the polymeric structure is simply a "gel" or a "hydrogel."

As used herein, the terms "guest-host chemistry" or "guest-host interaction" refer to a concept in supramolecular chemistry whereby a complex is formed between two or more molecules or ions, held together by forces other than covalent bonds. In certain embodiments, the two or more molecules or ions are held together by a force selected from but not limited to hydrogen bonds, ionic bonds, van der Waals forces, hydrophobic interactions, hydrophilic interactions and steric interaction. "Guest-host" interactions are also commonly referred to as "host-guest" interactions and the two terms are to be understood as equivalent herein.

As used herein, the term "microsphere" refers to a spherical or spheroid particle with a diameter in the range of about 0.5 μm to about 1 mm. In certain embodiments, microspheres comprise one or more layers, optionally including an outer shell layer, while in other embodiments, microspheres do not comprise layers or an outer shell.

As used herein, the term "monodisperse" refers to a particle based composition comprising particles that are substantially uniform in size, shape and mass. In certain embodiments, a monodisperse composition of microspheres contains particles of nearly the same size, forming a narrow distribution about an average value, whereas a polydisperse suspension contains particles of different sizes, forming a broad distribution.

In certain embodiments, monodisperse or near-monodisperse particles have equal to or less than about 15% coefficient of variation. In other embodiments, monodisperse particles have equal to or less than about 5% coefficient of variation (that is, $CV=\sigma/d<5\%$, where $\sigma$ and $d$ are the standard deviation and the mean size, respectively). In yet other embodiments, the monodisperse particles have equal to or less than about 5%, 2%, or 1%.

As used herein, the term "patient," "individual" or "subject" refers to a human or a non-human mammal. Non-human mammals include, for example, livestock and pets, such as ovine, bovine, porcine, canine, feline and murine mammals. Preferably, the patient, individual or subject is human.

As used herein, the term "pharmaceutically acceptable" refers to a material, such as a carrier or diluent, which does not abrogate the biological activity or properties of the compound, and is relatively non-toxic, i.e., the material may be administered to an individual without causing undesirable biological effects or interacting in a deleterious manner with any of the components of the composition in which it is contained.

As used herein, the term "pharmaceutically acceptable carrier" means a pharmaceutically acceptable material, composition or carrier, such as a liquid or solid filler, stabilizer, dispersing agent, suspending agent, diluent, excipient, thickening agent, solvent or encapsulating material, involved in carrying or transporting a compound useful within the invention within or to the patient such that it may perform its intended function. Each carrier must be "acceptable" in the sense of being compatible with the other ingredients of the formulation, including the compound useful within the invention, and not injurious to the patient. Some examples of materials that may serve as pharmaceutically acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; surface active agents; alginic acid; pyrogen-free water; isotonic saline; Ringer's solution; ethyl alcohol; phosphate buffer solutions; and other non-toxic compatible substances employed in pharmaceutical formulations.

As used herein, "pharmaceutically acceptable carrier" also includes any and all coatings, antibacterial and antifungal agents, and absorption delaying agents, and the like that are compatible with the activity of the compound useful within the invention, and are physiologically acceptable to the patient. Supplementary active compounds may also be incorporated into the compositions. The "pharmaceutically acceptable carrier" may further include a pharmaceutically acceptable salt of the compound useful within the invention. Other additional ingredients that may be included in the pharmaceutical compositions used in the practice of the invention are known in the art and described, for example in Remington's Pharmaceutical Sciences (Genaro, Ed., Mack Publishing Co., 1985, Easton, Pa.), which is incorporated herein by reference.

As used herein, the language "pharmaceutically acceptable salt" refers to a salt of the administered compounds prepared from pharmaceutically acceptable non-toxic acids, including inorganic acids, organic acids, solvates, hydrates, or clathrates thereof.

The term "prevent," "preventing" or "prevention," as used herein, means avoiding or delaying the onset of symptoms associated with a disease or condition in a subject that has not developed such symptoms at the time the administering of an agent or compound commences.

A "therapeutic" treatment is a treatment administered to a subject who exhibits signs of pathology, for the purpose of diminishing or eliminating those signs.

As used herein, the term "treatment" or "treating" is defined as the application or administration of a therapeutic agent, i.e., a compound of the invention (alone or in combination with another pharmaceutical agent), to a patient, or application or administration of a therapeutic agent to an isolated tissue or cell line from a patient (e.g., for diagnosis or ex vivo applications), who has a condition contemplated herein, a symptom of a condition contemplated herein or the potential to develop a condition contemplated herein, with the purpose to cure, heal, alleviate, relieve, alter, remedy, ameliorate, improve or affect a condition contemplated herein, the symptoms of a condition contemplated herein or the potential to develop a condition contemplated herein. Treatment may also comprise application or administration of a therapeutic to an allograph tissue or cells or xenograph tissue or cells followed by application or administration of the allograph or xenograph tissues or cells to a patient who has a condition contemplated herein, with the purpose to cure, heal, alleviate, relieve, alter, remedy, ameliorate, improve or affect a condition contemplated herein, the symptoms of a condition contemplated herein or the potential to develop a condition contemplated herein. Such treatments may be specifically tailored or modified, based on knowledge obtained from the field of pharmacogenomics.

As used herein, the term "therapeutically effective amount" refers to an amount that is sufficient or effective to prevent or treat (delay or prevent the onset of, prevent the progression of, inhibit, decrease or reverse) a disease or condition described or contemplated herein, including alleviating symptoms of such disease or condition.

Throughout this disclosure, various aspects of the invention may be presented in a range format. It should be understood that the description in range format is merely for convenience and brevity and should not be construed as an inflexible limitation on the scope of the invention. Accordingly, the description of a range should be considered to have specifically disclosed all the possible sub-ranges as well as individual numerical values within that range and, when appropriate, partial integers of the numerical values within ranges. For example, description of a range such as from 1 to 6 should be considered to have specifically disclosed sub-ranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

The following abbreviations are used herein:
Alg alginate
Alg-MA alginate methacrylate
β-CD βcyclodextrin
CRGDS Cys-Arg-Gly-Asp-Ser peptide
hep heparin
hMSC human mesenchymal stem cells
MA methacrylate
MEM Minimum Essential Medium
PEG poly(ethylene glycol)
PEO poly(ethylene oxide)
PPG poly(propylene glycol)
RGD arginylglycylaspartic acid Compositions In one aspect, the invention provides a hydrogel composition comprising alginate (Alg) or methacrylated alginate (Alg-MA), and β-cyclodextrin (β-CD) further comprising at least one selected from the group consisting of heparin (hep) and arginylglycylaspartic acid (RGD). In certain embodiments, the β-CD is covalently bound to the alginate backbone.

In certain embodiments, the heparin is covalently bound to at least one selected from the group consisting of alginate (Alg-Hep), methacrylated alginate (Alg-MA-hep), β-cyclodextrin modified alginate (Alg-β-CD-hep) and methacrylated and β-cyclodextrin modified alginate (Alg-MA-β-CD-hep). In other embodiments, the arginylglycylaspartic acid (RGD) is covalently bound to at least one selected from the group consisting of alginate (Alg-RGD), methacrylated alginate (Alg-MA-RGD), β-cyclodextrin modified alginate (Alg-β-CD-RGD) and methacrylated and β-cyclodextrin modified alginate (Alg-MA-β-CD-RGD). In yet other embodiments, the hydrogel composition comprises at least one covalently bound composition selected from the group consisting of (Alg-MA-β-CD), (Alg-MA-β-CD-hep), (Alg-MA-β-CD-RGD), (Alg-MA-β-CD-hep-RGD), (Alg-β-CD), (Alg-β-CD-hep), (Alg-β-CD-RGD), and (Alg-β-CD-hep-RGD).

In certain embodiments, the hydrogel further comprises at least one additional component selected from the group consisting of polypropylene glycol (PPG), polyethylene glycol (PEG), polyethylene oxide (PEO), PEG-b-PPG-b-PEG copolymers, PEO-b-PPG-b-PEO copolymers, agarose, amylase, amylpectin, cellularose, chitosan, collagen, fibrin, gelatin, glycogenhyaluronic acid, poly(acrylamide), poly(β-aminoester), poly(caprolactone), matrigel, multi-arm polyethylene glycol, poly-hydroxyethyl acrylate, poly(hydroxyethyl methacrylate), poly(N-isopropylacrylamide), poly(glycolic acid), poly(lactic acid), poly(lactic acid-glycolic acid), oligo(poly(ethylene glycol)fumarate), poly(vinyl alcohol), poly(vinyl acid), 1-ethyl-3-[3-dimethylaminopropyl] carbodiimide hydrochloride (EDC), and N-hydroxysuccinimide (NHS). In other embodiments, the at least one additional component is covalently bound to at least one selected from the group consisting of Alg, Alg-MA, Alg-Hep, Alg-MA-hep, Alg-β-CD, Alg-β-CD-hep, Alg-MA-β-CD-hep, Alg-RGD, Alg-MA-RGD, Alg-β-CD-RGD, and Alg-MA-β-CD-RGD. In certain embodiments, the at least one additional component is amphilic. In other embodiments, the at least one additional component is chemically modified (e.g., methacrylated, conjugated with guest:host molecules, thiol, disulfide, ect. functional group additions) to allow for crosslinking (e.g., covalent, ionic, and hydrogen bond formation between polymer chains) to form a hydrogel. In certain embodiments, the incorporation of the at least one additional component allows for the formation of a supramolecular network.

In certain embodiments, the hydrogel composition further comprises at least one kind of living cell. In other embodiments, the at least one kind of living cell is encapsulated within the hydrogel composition. In yet other embodiments, the at least one kind of living cell is a eukaryotic cell. In yet other embodiments, the at least one kind of living cell is a mammalian cell. In yet other embodiments, the at least one living cell is selected from, but not necessarily limited to, the group consisting of stem cells, embryonic cells and fully differentiated cells. In yet other embodiments, the living cells are human mesenchymal stem cells. In certain embodiments, the hydrogel composition supports and maintains the viability of cells encapsulated therein for at least 72 hours. In other embodiments, the hydrogel composition supports the development of vasculature structure for cells encapsulated therein. Without wishing to be limited to any particular theory, the hydrogel composition promotes vascularization due to the fact that the conjugated heparin molecules bind and retain a variety of growth factors, such as, but not limited to, platelet derived growth factor (PDGF), epidermal growth factor (EGF), hepatocyte growth factor (HGF), vascular endothelial growth factor (VEGF) and basic fibroblast growth factor (bFGF). In certain embodiments, the hydrogel composition promotes the differentiation of cells embedded therein. Without intending to be limited to any particular theory, in certain embodiments, the hydrogel composition promotes the differentiation of cells embedded therein, at least in part, due to the hep and RGD conjugation, and delivery of heparin-binding proteins. In other embodiments, heparin conjugation allows for the the selection and retention of various heparin-binding growth factors, including those described herein.

In certain embodiments, the hydrogel composition further comprises at least one pharmaceutically active compound. In other embodiments, the pharmaceutically active compound is encapsulated within the hydrogel composition. In yet other embodiments, the at least one pharmaceutically active compound is any pharmaceutically active compound known in the art. In certain embodiments, the at least one pharmaceutically active compound is selected from the group consisting of oligonucelotides, proteins, polysaccharides, sugars, lipids, exosomes, cholesterols, and anti-cancer agents. In other embodiments, the at least one pharmaceutically active compound is an amphiphilic compound. In yet other embodiments, the at least one pharmaceutically active compound is an acidic or basic compound. In certain embodiments, the pharmaceutically active compound is bound to the hydrogel composition through a guest-host interaction with the β-CD moieties. In certain embodiments, the pharmaceutically active compound is bound to the hydrogel composition through a heparin-binding site on a heparin-modified alginate material.

In certain embodiments, the hydrogel composition further comprises at least one biological factor. In other embodiments, the at least one biological factor modifies one or more cellular functions selected from the group consisting of cell growth, cell viability, cell adhesion, tissue adhesion, and progenitor cell differentiation. In other embodiments, the hydrogel composition further comprises at least one biological factor selected from the group consisting of growth factors, such as, but not limited to, heparin-binding proteins. In yet other embodiments, the hydrogel composition further comprises at least one biological factor selected from the group consisting of epidermal growth factor (EGF), platelet derived growth factor (PDGF), basic fibroblast growth factor (bFGF), transforming growth factor-beta (TGF-β), and tissue inhibitors of metalloproteinases (TIMP).

In certain embodiments, the hydrogel composition is in the form of a microsphere composition. In other embodiments, the microspheres are monodisperse microspheres. In yet other embodiments, the microspheres have a diameter of about 500 nm to about 80 μm. In yet other embodiments, the microspheres can be fabricated through any methods known in the art, including, but not limited to, the use of a microfluidics device, water/oil emulsions, and the use of electrostatic droplet generation.

In certain embodiments, the hydrogel composition is in the form of a bulk material. In other embodiments, the hydrogel composition has a particle size diameter greater than about 80 μm.

In certain embodiments, the hydrogel composition is formulated as part of a pharmaceutical composition in the form of a cream, liquid, gel, spray, ointment or the like. In certain embodiments, the pharmaceutical composition further comprising at least one pharmaceutically acceptable carrier. In certain embodiments, the pharmaceutical composition comprises microspheres of the hydrogel composition.

In certain embodiments, the hydrogel composition is in the form of a hydrogel polymer solution wherein the Alg or chemically-modified alginate are not crosslinked. In other embodiments, the hydrogel polymer solution is a pre-cursor polymer solution that can be crosslinked to form a hydrogel of the invention. In other embodiments, the hydrogel polymer solution demonstrates shear-thinning properties, wherein the composition behaves as a non-Newtonian fluid, demonstrating decreased viscosity under shear strain. In yet other embodiments, the non-crosslinked hydrogel polymer solution can be crosslinked through the use of at least one curing methods, including but not limited to exposure to light, exposure to heat and the addition of a curing agent compound or crosslinking agent. In other embodiments, the non-crosslinked hydrogel polymer solution can be a flowable composition that allows the solution to first penetrate a substrate material and then be crosslinked as discussed elsewhere herein. In certain embodiments, the hydrogel composition further comprises at least one crosslinking agent. In other embodiments, the crosslinking initiator is a photoinitiator. In yet other embodiments, the crosslinking agent is selected from the group consisting of eosin Y, triethanolamine, and 1-vinyl-2-pyrrolidinone. In certain embodiments, the crosslinking agent is an ionic crosslinking agent such as a divalent metal cation. In other embodiments, the crosslinking agent is a calcium salt. In yet other embodiments, the crosslinking agent is calcium chloride.

In certain embodiments, the hydrogel composition is in the form of a crosslinked polymer comprising a hydrogel composition and a pharmaceutically acceptable solvent. In other embodiments, the hydrogel polymer and/or the hydrogel polymer solution, have sufficiently low shearing modulus that it can be manipulated through the use of a syringe.

In certain embodiments, the hydrogel composition is in the form of a hydrogel cream, liquid, gel, spray, ointment, 3-D scaffold, patch or graft for use in dressing wounds in a subject. In other embodiments, the hydrogel composition is disposed on the surface of a wound dressing substrate such as a patch, bandage or graft. In yet other embodiments, the hydrogel composition is formed on the surface of a wound.

In certain embodiments, the hydrogel composition is in the form of a hydrogel cream, liquid, gel, spray, ointment, 3-D scaffold, patch or graft for use in delivering at least one pharmaceutically active compound. In other embodiments, the patch is formulated as a dehydrated polymer patch or hydrogel patch. In other embodiments, the hydrogel composition is in the form of a patch or graft adapted and configured to topically deliver at least one pharmaceutically active compound to a subject.

In certain embodiments, the hydrogel composition is in the form of a hydrogel or hydrogel polymer solution, cream, liquid, gel, spray, ointment, 3-D scaffold, patch or graft for use in delivering at least one biological agents, including a living cell or a biological factor.

In certain embodiments, the hydrogel composition is a self-healing hydrogel.

In certain embodiments, the hydrogel composition is a biodegradable hydrogel. In other embodiments, the hydrogel composition is a non-biodegradable hydrogel.

Methods

In one aspect, the invention provides a method of treating diseases and disorders in a subject in need thereof, the method comprising administering a hydrogel composition of the invention to the subject.

In one aspect, the invention provides a method of delivering viable living cells to a subject, the method comprising administering to the subject a hydrogel composition of the invention comprising encapsulated viable living cells. In certain embodiments, the delivery of viable living cells treats at least one disease or disorder in the subject selected from the group consisting of immune-mediated diseases, skeletal/cranial tissue injury, skeletal diseases (such as osteoporosis), skin wounds, internal wounds to an organ coating or a portion of an organ/tissue, cancers, inflammatory diseases such as diabetes or arthritis, infections, and chronic wounds (such as ulcers). In certain embodiments, a hydrogel or hydrogel polymer solution comprising viable living cells is administered to the subject in a non-crosslinked, highly flowable form and is then crosslinked after administration, thereby forming the hydrogel composition.

In another aspect, the invention provides a method of delivering a pharmaceutically active compound to a subject, the method comprising administering to the subject a hydrogel composition of the invention comprising an encapsulated pharmaceutically active compound.

In yet another aspect, the invention provides a method of treating a wound in a subject in need thereof, the method comprising contacting the wound with a hydrogel composition of the invention comprising encapsulated viable living cells. In certain embodiments, the hydrogel composition is in the form of a patch or graft. In other embodiments, the hydrogel or hydrogel polymer solution composition is disposed on the surface of a wound dressing substrate such as a bandage, patch or graft. In certain embodiments, the wound is at least one selected from the group consisting of a skin wound, a bone wound, a connective tissue wound, a membrane wound, damage to an organ or lining of an organ, inflammation, and infection. In certain embodiments, a hydrogel polymer solution comprising viable living cells is contacted to the subject in a non-crosslinked, highly flowable form and is then crosslinked after contacting, thereby forming the hydrogel composition.

Combination and Concurrent Therapies

In one embodiment, the compositions of the invention are useful in the methods of present invention when used concurrently with at least one additional compound useful for preventing and/or treating diseases and/or disorders contemplated herein.

In one embodiment, the compositions of the invention are useful in the methods of present invention in combination with at least one additional compound useful for preventing and/or treating diseases and/or disorders contemplated herein.

These additional compounds may comprise compounds of the present invention or other compounds, such as commercially available compounds, known to treat, prevent, or reduce the symptoms of diseases and/or disorders contemplated herein. In certain embodiments, the combination of at least one compound of the invention or a salt thereof, and at least one additional compound useful for preventing and/or treating diseases and/or disorders contemplated herein, has additive, complementary or synergistic effects in the prevention and/or treatment of diseases and/or disorders contemplated herein.

As used herein, combination of two or more compounds may refer to a composition wherein the individual compounds are physically mixed or wherein the individual compounds are physically separated. A combination therapy encompasses administering the components separately to produce the desired additive, complementary or synergistic effects.

Administration/Dosage/Formulations

The regimen of administration may affect what constitutes an effective amount. The therapeutic formulations may be administered to the subject either prior to or after the onset of a disease or disorder contemplated in the invention. Further, several divided dosages, as well as staggered dosages may be administered daily or sequentially, or the dose may be continuously infused, or may be a bolus injection. Further, the dosages of the therapeutic formulations may be proportionally increased or decreased as indicated by the exigencies of the therapeutic or prophylactic situation.

Administration of the compositions of the present invention to a patient, preferably a mammal, more preferably a human, may be carried out using known procedures, at dosages and for periods of time effective to treat a disease or disorder contemplated in the invention. An effective amount of the therapeutic compound necessary to achieve a therapeutic effect may vary according to factors such as the state of the disease or disorder in the patient; the age, sex, and weight of the patient; and the ability of the therapeutic compound to treat a disease or disorder contemplated in the invention. Dosage regimens may be adjusted to provide the optimum therapeutic response. For example, several divided doses may be administered daily or the dose may be proportionally reduced as indicated by the exigencies of the therapeutic situation. A non-limiting example of an effective dose range for a therapeutic compound of the invention is from about 1 and 5,000 mg/kg of body weight/per day. One of ordinary skill in the art would be able to study the relevant factors and make the determination regarding the effective amount of the therapeutic compound without undue experimentation.

Actual dosage levels of the active ingredients in the pharmaceutical compositions of this invention may be varied so as to obtain an amount of the active ingredient that is effective to achieve the desired therapeutic response for a particular patient, composition, and mode of administration, without being toxic to the patient.

The therapeutically effective amount or dose of a compound of the present invention depends on the age, sex and weight of the patient, the current medical condition of the patient and the progression of a disease or disorder contemplated in the invention.

A medical doctor, e.g., physician or veterinarian, having ordinary skill in the art may readily determine and prescribe the effective amount of the pharmaceutical composition required. For example, the physician or veterinarian could start doses of the compounds of the invention employed in the pharmaceutical composition at levels lower than that required in order to achieve the desired therapeutic effect and gradually increase the dosage until the desired effect is achieved.

A suitable dose of a compound of the present invention may be in the range of from about 0.01 mg to about 5,000 mg per day, such as from about 0.1 mg to about 1,000 mg, for example, from about 1 mg to about 500 mg, such as about 5 mg to about 250 mg per day. The dose may be administered in a single dosage or in multiple dosages, for example from 1 to 4 or more times per day. When multiple dosages are used, the amount of each dosage may be the same or different. For example, a dose of 1 mg per day may be administered as two 0.5 mg doses, with about a 12-hour interval between doses.

Compounds of the invention for administration may be in the range of from about 1 µg to about 10,000 mg, about 20 µg to about 9,500 mg, about 40 µg to about 9,000 mg, about 75 µg to about 8,500 mg, about 150 µg to about 7,500 mg, about 200 µg to about 7,000 mg, about 300 µg to about 6,000 mg, about 500 µg to about 5,000 mg, about 750 µg to about 4,000 mg, about 1 mg to about 3,000 mg, about 10 mg to about 2,500 mg, about 20 mg to about 2,000 mg, about 25 mg to about 1,500 mg, about 30 mg to about 1,000 mg, about 40 mg to about 900 mg, about 50 mg to about 800 mg, about 60 mg to about 750 mg, about 70 mg to about 600 mg, about 80 mg to about 500 mg, and any and all whole or partial increments there between.

In some embodiments, the dose of a compound of the invention is from about 1 mg and about 2,500 mg. In some embodiments, a dose of a compound of the invention used in compositions described herein is less than about 10,000 mg, or less than about 8,000 mg, or less than about 6,000 mg, or less than about 5,000 mg, or less than about 3,000 mg, or less than about 2,000 mg, or less than about 1,000 mg, or less than about 500 mg, or less than about 200 mg, or less than about 50 mg. Similarly, in some embodiments, a dose of a second compound as described herein is less than about 1,000 mg, or less than about 800 mg, or less than about 600 mg, or less than about 500 mg, or less than about 400 mg, or less than about 300 mg, or less than about 200 mg, or less than about 100 mg, or less than about 50 mg, or less than about 40 mg, or less than about 30 mg, or less than about 25 mg, or less than about 20 mg, or less than about 15 mg, or less than about 10 mg, or less than about 5 mg, or less than about 2 mg, or less than about 1 mg, or less than about 0.5 mg, and any and all whole or partial increments thereof.

In one embodiment, the compositions of the invention are administered to the patient in dosages that range from one to five times per day or more. In another embodiment, the compositions of the invention are administered to the patient in range of dosages that include, but are not limited to, once every day, every two, days, every three days to once a week, and once every two weeks. It is readily apparent to one skilled in the art that the frequency of administration of the various combination compositions of the invention varies from individual to individual depending on many factors including, but not limited to, age, disease or disorder to be treated, gender, overall health, and other factors. Thus, the invention should not be construed to be limited to any particular dosage regime and the precise dosage and composition to be administered to any patient is determined by the attending physical taking all other factors about the patient into account.

It is understood that the amount of compound dosed per day may be administered, in non-limiting examples, every day, every other day, every 2 days, every 3 days, every 4 days, or every 5 days. For example, with every other day administration, a 5 mg per day dose may be initiated on Monday with a first subsequent 5 mg per day dose administered on Wednesday, a second subsequent 5 mg per day dose administered on Friday, and so on.

In the case wherein the patient's status does improve, upon the doctor's discretion the administration of the inhibitor of the invention is optionally given continuously; alternatively, the dose of drug being administered is temporarily reduced or temporarily suspended for a certain length of time (i.e., a "drug holiday"). The length of the drug holiday optionally varies between 2 days and 1 year, including by way of example only, 2 days, 3 days, 4 days, 5 days, 6 days, 7 days, 10 days, 12 days, 15 days, 20 days, 28 days, 35 days, 50 days, 70 days, 100 days, 120 days, 150 days, 180 days, 200 days, 250 days, 280 days, 300 days, 320 days, 350 days, or 365 days. The dose reduction during a drug holiday includes from 10%-100%, including, by way of example only, 10%, 15%, 20%, 25%, 30%, 35%, 40%, 45%, 50%, 55%, 60%, 65%, 70%, 75%, 80%, 85%, 90%, 95%, or 100%.

Once improvement of the patient's conditions has occurred, a maintenance dose is administered if necessary. Subsequently, the dosage or the frequency of administration, or both, is reduced, as a function of the disease or disorder, to a level at which the improved disease is retained. In one embodiment, patients require intermittent treatment on a long-term basis upon any recurrence of symptoms and/or infection.

The compounds for use in the method of the invention may be formulated in unit dosage form. The term "unit dosage form" refers to physically discrete units suitable as unitary dosage for patients undergoing treatment, with each unit containing a predetermined quantity of active material calculated to produce the desired therapeutic effect, optionally in association with a suitable pharmaceutical carrier. The unit dosage form may be for a single daily dose or one of multiple daily doses (e.g., about 1 to 4 or more times per day). When multiple daily doses are used, the unit dosage form may be the same or different for each dose.

Toxicity and therapeutic efficacy of such therapeutic regimens are optionally determined in cell cultures or experimental animals, including, but not limited to, the determination of the $LD_{50}$ (the dose lethal to 50% of the population) and the $ED_{50}$ (the dose therapeutically effective in 50% of the population). The dose ratio between the toxic and therapeutic effects is the therapeutic index, which is expressed as the ratio between $LD_{50}$ and $ED_{50}$. The data obtained from cell culture assays and animal studies are optionally used in formulating a range of dosage for use in human. The dosage of such compounds lies preferably within a range of circulating concentrations that include the $ED_{50}$ with minimal toxicity. The dosage optionally varies within this range depending upon the dosage form employed and the route of administration utilized.

In one embodiment, the compositions of the invention are formulated using at least one pharmaceutically acceptable excipients or carriers. In one embodiment, the pharmaceutical compositions of the invention comprise a therapeutically effective amount of a compound of the invention and a pharmaceutically acceptable carrier.

The pharmaceutical compositions may be sterilized and if desired mixed with auxiliary agents, e.g., lubricants, preservatives, stabilizers, wetting agents, emulsifiers, salts for influencing osmotic pressure buffers, coloring, and/or aromatic substances and the like.

The carrier may be a solvent or dispersion medium containing, for example, water, ethanol, polyol (for example, glycerol, propylene glycol, and liquid polyethylene glycol, and the like), suitable mixtures thereof, and vegetable oils. The proper fluidity may be maintained, for example, by the use of a coating such as lecithin, by the maintenance of the required particle size in the case of dispersion and by the use of surfactants. Prevention of the action of microorganisms may be achieved by various antibacterial and antifungal agents, for example, parabens, chlorobutanol, phenol, ascorbic acid, thimerosal and the like. In many cases, it is preferable to include isotonic agents, for example, sugars, sodium chloride, or polyalcohols such as mannitol and sorbitol, in the composition.

In one embodiment, the present invention is directed to a packaged pharmaceutical composition comprising a container holding a therapeutically effective amount of a compound of the invention, alone or in combination with a second pharmaceutical agent; and instructions for using the compound to treat, prevent, or reduce at least one symptoms of a disease or disorder contemplated in the invention.

Formulations may be employed in admixtures with conventional excipients, i.e., pharmaceutically acceptable organic or inorganic carrier substances suitable for any suitable mode of administration, known to the art. The pharmaceutical preparations may be sterilized and if desired mixed with auxiliary agents, e.g., lubricants, preservatives, stabilizers, wetting agents, emulsifiers, salts for influencing osmotic pressure buffers, coloring, flavoring and/or aromatic substances and the like. They may also be combined where desired with other active agents, e.g., analgesic agents.

Routes of administration of any of the compositions of the invention include inhalational, oral, nasal, rectal, parenteral, sublingual, transdermal, transmucosal (e.g., sublingual, lingual, (trans)buccal, (trans)urethral, vaginal (e.g., trans- and perivaginally), (intra)nasal, and (trans)rectal), intravesical, intrapulmonary, intraduodenal, intragastrical, intrathecal, epidural, intrapleural, intraperitoneal, intratracheal, otic, intraocular, subcutaneous, intramuscular, intradermal, intraarterial, intravenous, intrabronchial, inhalation, and topical administration. In certain embodiments, routes of administration of any of the compositions of the invention include nasal, inhalational, intratracheal, intrapulmonary, and intrabronchial.

Suitable compositions and dosage forms include, for example, dispersions, suspensions, solutions, syrups, granules, beads, powders, pellets, liquid sprays for nasal or oral administration, dry powder or aerosolized formulations for inhalation, and the like. It should be understood that the formulations and compositions that would be useful in the present invention are not limited to the particular formulations and compositions that are described herein.

Powdered and granular formulations of a pharmaceutical preparation of the invention may be prepared using known methods. Such formulations may be administered directly to a subject, used, for example, to form a material that is suitable to administration to a subject. Each of these formulations may further comprise at least one of dispersing or wetting agent, a suspending agent, and a preservative. Additional excipients, such as fillers and sweetening, flavoring, or coloring agents, may also be included in these formulations.

Those skilled in the art will recognize, or be able to ascertain using no more than routine experimentation, numerous equivalents to the specific procedures, embodiments, claims, and examples described herein. Such equivalents were considered to be within the scope of this invention and covered by the claims appended hereto. For example, it should be understood, that modifications in reaction conditions, including but not limited to reaction times, reaction size/volume, and experimental reagents, such as solvents, catalysts, pressures, atmospheric conditions, e.g., nitrogen atmosphere, and reducing/oxidizing agents, with art-recognized alternatives and using no more than routine experimentation, are within the scope of the present application.

It is to be understood that, wherever values and ranges are provided herein, the description in range format is merely for convenience and brevity and should not be construed as an inflexible limitation on the scope of the invention. Accordingly, all values and ranges encompassed by these values and ranges are meant to be encompassed within the scope of the present invention. Moreover, all values that fall within these ranges, as well as the upper or lower limits of a range of values, are also contemplated by the present application. The description of a range should be considered to have specifically disclosed all the possible sub-ranges as well as individual numerical values within that range and, when appropriate, partial integers of the numerical values within ranges. For example, description of a range such as from 1 to 6 should be considered to have specifically disclosed sub-ranges such as from 1 to 3, from 1 to 4, 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

The following examples further illustrate aspects of the present invention. However, they are in no way a limitation of the teachings or disclosure of the present invention as set forth herein.

EXAMPLES

The invention is now described with reference to the following Examples. These Examples are provided for the purpose of illustration only, and the invention is not limited to these Examples, but rather encompasses all variations that are evident as a result of the teachings provided herein.

Materials and Methods

Sodium alginate (PROTANAL® LF200 FTS, My=67-142 kg/mol) was kindly donated by FMC Biopolymer. Methacrylic anhydride, calcium chloride ($CaCl_2$), N-ethyl-N'(3-dimethylaminopropyl) carbodiimide hydrochloric acid (EDC), N-hydroxysuccinimide (NETS), Pluronic® F-127 [poly(ethylene oxide)-block-polypropylene oxide)-block-poly(ethylene oxide), PEO-b-PPG-b-PEO, Mn=13 kg/mol], triethanolamine, eosin Y, 1-vinyl-2-pyrrolidinonewere, and heparin sodium salt from porcine intestinal mucosa (Hep) was purchased from Sigma Aldrich. Beta-cyclodextrin (β-CD), p-toluenesulfonyl chloride (TosCl), acetonitrile, acetone, and ethylenediamine (EDA) were purchased from Acros Organics. Sodium hydroxide (NaOH), ammonium chloride ($NH_4Cl$), hydrogen chloride (HCl), phosphate buffered saline (PBS), and 2-morpholinoethanesulfonic acid (MES) buffer were purchased from Thermo Fisher Scientific. Arg-Gly-Asp-Cys (RGD) (molecular weight: 449.48) was purchased at Genscript Catalog.

β-cyclodextrin-Ethylenediamine (β-CD-EDA)

β-CD (20 g) was dissolved in cold DI water, and TosCl (4.2 g) was dissolved in 10 mL of acetonitrile. The TosCl solution was added dropwise to the β-CD solution, and vigorously stirred for 2 hours at room temperature. NaOH (2.18 g) was dissolved in 10 mL of DI water, added dropwise to the β-CD solution, and vigorously stirred for 30 minutes at room temperature. Solid $NH_4Cl$ was added to adjust the pH to approximately 8.5. The solution was placed in the refrigerator overnight, and the precipitate, β-CD-TosCl, was washed with DI water and acetone (3× each), and dried under vacuum. β-CD-TosCl (1.5 g) was added to 5 mL of EDA and stirred under a condenser at 60° C. for 24 hours. Solution was cooled to room temperature then precipitated in cold ethanol. The precipitate (β-CD-EDA) was washed five times with ethanol and dried under vacuum to yield a dry polymer.

One Modification:

Alg-MA Synthesis

Sodium alginate was dissolved in PBS to create a 1% (w/v) solution at room temperature. A 10-fold molar excess of methacrylic anhydride was added to the alginate solution. The pH of the solution was periodically adjusted to 8.5-10, using 5N NaOH, and the methacrylation reaction was carried out for 12-36 hours, depending on desired degree of modification. The final pH was adjusted to 7 using 5N NaOH. The methacrylated alginate (Alg-MA) solution was purified via dialysis (MWCO=6-8 kDa) against deionized water for three-five days, and lyophilized to yield a dry product.

Alg-β-CD Synthesis

Alg (3.0 g) was dissolved in 0.1M MES buffer (pH 5.6, 150 mL), to which EDC (2 g) and NHS (1.2 g) were added. After mixing for 30 minutes at room temperature, β-CD-EDA (4.5 g) was added under vigorous mixing at room temperature for one day. The Alg-β-CD solution was purified via dialysis (MWCO=6-8 kDa) against deionized water for three-five days, and lyophilized to yield a dry product.

Alg-RGD Synthesis

Alg (0.5 g) was dissolved in 0.1M MES buffer (pH 5.6, 25 mL), to which EDC (0.33 g) and NHS (0.2 g) were added. After mixing for 30 minutes at room temperature, RGD (5 mg) was added and mixed vigorously at room temperature for 24 hours. The Alg-RGD solution was purified via dialysis (MWCO=6-8 kDa) against deionized water for three-five days, and lyophilized to yield a dry product.

Alg-Hep Synthesis

Heparin sodium salt (Hep) (0.25 g) was slowly dissolved in 0.1M MES buffer (pH 5.6, 12.5 mL). N-ethyl-N'(3-dimethylaminopropyl) carbodiimide hydrochloric acid (EDC) (0.042 g) was added to Hep solution followed by N-hydroxysuccinimide (NHS) (0.07 g). The reaction was allowed to stir at room temperature for 24 hours. A 20 molar excess of ethylenediamine (EDA) (1.11 ml) was added and the reaction was stirred overnight in an ice bath. The product (Hep-EDA) was dried under vacuum. Sodium alginate (Alg) (0.25 g) was slowly dissolved in 0.1M MES buffer (pH 5.6, 12.5 mL). N-ethyl-N'(3-dimethylaminopropyl) carbodiimide hydrochloric acid (EDC) (0.22 g) was added to Alg solution followed by N-hydroxysuccinimide (NETS) (0.13 g). The reaction was allowed to stir at room temperature for 24 hours. The dried Hep-EDA was dissolved in 10 ml of DI water and added to alginate solution and allowed to stir at room temperature for 24 hours. The Alg-Hep solution was purified via dialysis (MWCO=6-8 kDa) against deionized water for three-five days, and lyophilized to yield a dry product.

Two Modifications:

Alg-MA-β-CD Synthesis

Alg-MA (3.0 g) was dissolved in 0.1 M MES buffer (pH 5.6, 150 mL), to which EDC (2 g) and NETS (1.2 g) were added. After mixing for 30 minutes at room temperature, β-CD-EDA (4.5 g) was added under vigorous mixing at room temperature for one day. The Alg-MA-β-CD solution was purified via dialysis (MWCO=6-8 kDa) against deionized water for three-five days, and lyophilized to yield a dry product.

Alg-MA-RGD Synthesis

Alg-MA (0.5 g) was dissolved in 0.1M MES buffer (pH 5.6, 25 mL), to which EDC (0.33 g) and NHS (0.2 g) were added. After mixing for 30 minutes at room temperature, RGD (5 mg) was added and mixed vigorously at room temperature for 24 hours. The Alg-MA-RGD solution was purified via dialysis (MWCO=6-8 kDa) against deionized water for three-five days, and lyophilized to yield a dry product.

Alg-MA-Hep Synthesis

Heparin sodium salt (Hep) (0.25 g) was slowly dissolved in 0.1M MES buffer (pH 5.6, 12.5 mL). N-ethyl-N'(3-dimethylaminopropyl) carbodiimide hydrochloric acid (EDC) (0.042 g) was added to Hep solution followed by N-hydroxysuccinimide (NHS) (0.07 g). The reaction was allowed to stir at room temperature for 24 hours. A 20 molar excess of ethylenediamine (EDA) (1.11 mL) was added and the reaction was stirred overnight in an ice bath. The product (Hep-EDA) was precipitated out of solution with excess cold acetonitrile and dried under vacuum. Methacrylated Sodium alginate (Alg-MA) (0.25 g) was slowly dissolved in 0.1 M MES buffer (pH 5.6, 12.5 mL). N-ethyl-N'(3-dimethylaminopropyl) carbodiimide hydrochloric acid (EDC) (0.22 g) was added to Alg solution followed by N-hydroxysuccinimide (NETS) (0.13 g). The reaction was allowed to stir at room temperature for 30 minutes at room temperature. The dried Hep-EDA was dissolved in 10 ml of DI water and added to alginate solution and allowed to stir at room temperature for 24 hours. The Alg-Hep solution was purified via dialysis (MWCO=6-8 kDa) against deionized water for three-five days, and lyophilized to yield a dry product.

Three Modifications:

Alg-MA-β-CD-RGD Synthesis

Alg-MA (0.5 g) was dissolved in 0.1 M MES buffer (pH 5.6, 25 mL), to which EDC (0.33 g) and NETS (0.2 g) were added and stirred for 30 minutes at room temperature. β-CD-EDA (0.75 g) was added under vigorous mixing at room temperature for one day. The Alg-MA-β-CD solution was purified via dialysis (MWCO=6-8 kDa) against deionized water for three-five days, and lyophilized to yield a dry product. Alg-MA-β-CD (0.5 g) was dissolved in 0.1M MES buffer (pH 5.6, 25 mL), to which EDC (0.33 g) and NETS (0.2 g) were added. After mixing for 30 minutes at room temperature, RGD (5 mg) was added an mixed vigorously at room temperature for one day. The Alg-MA-β-CD-RGD solution was purified via dialysis (MWCO=6-8 kDa) against deionized water for three-five days, and lyophilized to yield a dry product.

Alg-MA-β-CD-Hep Synthesis (Option A) [β-CD then Hep]

Heparin sodium salt (Hep) (0.25 g) was slowly dissolved in 0.1 M MES buffer (pH 5.6, 12.5 mL). N-ethyl-N'(3-dimethylaminopropyl) carbodiimide hydrochloric acid (EDC) (0.042 g) was added to Hep solution followed by N-hydroxysuccinimide (NHS) (0.07 g). The reaction was allowed to stir at room temperature for 24 hours. A 20 molar excess of ethylenediamine (EDA) (1.11 mL) was added and the reaction was stirred overnight in an ice bath. The product (Hep-EDA) was dried under vacuum. Methacrylated Sodium alginate (Alg-MA) (0.25 g) was slowly dissolved in 145.28 mL of DI water. N-ethyl-N'(3-dimethylaminopropyl) carbodiimide hydrochloric acid (EDC) (0.22 g) was added to Alg-MA solution followed by N-hydroxysuccinimide (NETS) (0.13 g). The reaction was allowed to stir at room temperature for 30 minutes. β-CD-EDA (0.375 g) was added under vigorous mixing at room temperature for one day. The Alg-MA-β-CD solution was purified via dialysis (MWCO=6-8 kDa) against deionized water for three-five days, and lyophilized to yield a dry product. Alg-MA-β-CD (0.5 g) was dissolved in 0.1 M MES buffer (pH 5.6, 25 mL), to which EDC (0.33 g) and NETS (0.2 g) were added and mixed for 30 minutes at room temperature. The dried Hep-EDA was dissolved in 10 mL of DI water and added to Alg-MA-β-CD solution and allowed to stir at room temperature for 24 hours. The Alg-MA-β-CD-Hep solution was purified via dialysis (MWCO=6-8 kDa) against deionized water for three-five days, and lyophilized to yield a dry product.

Alg-MA-β-CD-Hep Synthesis (Option B) [Hep then β-CD]

Heparin sodium salt (Hep) (0.25 g) was slowly dissolved in 0.1M MES buffer (pH 5.6, 12.5 mL). N-ethyl-N'(3-dimethylaminopropyl) carbodiimide hydrochloric acid (EDC) (0.042 g) was added to Hep solution followed by N-hydroxysuccinimide (NETS) (0.07 g). The reaction was allowed to stir at room temperature for 24 hours. A 20 molar excess of ethylenediamine (EDA) (1.11 ml) was added and the reaction was stirred overnight in an ice bath. The product (Hep-EDA) was dried under vacuum. Methacrylated Sodium alginate (Alg-MA) (0.25 g) was slowly dissolved in 0.1M MES buffer (pH 5.6, 12.5 mL). N-ethyl-N'(3-dimethylaminopropyl) carbodiimide hydrochloric acid (EDC) (0.22 g) was added to Alg-MA solution followed by N-hydroxysuccinimide (NHS) (0.13 g). The reaction was allowed to stir at room temperature for 30 minutes. The dried Hep-EDA was dissolved in 10 ml of DI water and added to alginate solution and allowed to stir at room temperature for 24 hours. The Alg-MA-Hep solution was purified via dialysis (MWCO=6-8 kDa) against deionized water for three-five days, and lyophilized to yield a dry product. Alg-MA-Hep (0.25 g) was dissolved in 0.1M MES buffer (pH 5.6, 25 mL), to which EDC (0.33 g) and NHS (0.2 g) were added and mixed for 30 minutes at room temperature. β-CD-EDA (0.375 g) was added under vigorous mixing at room temperature for one day. The Alg-MA-β-CD-Hep solution was purified via dialysis (MWCO=6-8 kDa) against deionized water for three-five days, and lyophilized to yield a dry product.

Four Modifications:

Alg-MA-β-CD-Hep-RGD Synthesis (Option A) [β-CD then Hep then RGD]

Alg-MA (0.25 g) was dissolved in 0.1M MES buffer (pH 5.6, 25 mL), to which EDC (0.33 g) and NHS (0.2 g) were added and mixed for 30 minutes at room temperature. β-CD-EDA (0.375 g) was added under vigorous mixing at room temperature for one day. The Alg-MA-β-CD solution was purified via dialysis (MWCO=6-8 kDa) against deionized water for three-five days, and lyophilized to yield a dry product. Heparin sodium salt (Hep) (0.25 g) was slowly dissolved in 0.1M MES buffer (pH 5.6, 12.5 mL). N-ethyl-N'(3-dimethylaminopropyl) carbodiimide hydrochloric acid (EDC) (0.042 g) was added to Hep solution followed by N-hydroxysuccinimide (NHS) (0.07 g). The reaction was allowed to stir at room temperature for 24 hours. A 20 molar excess of ethylenediamine (EDA) (1.11 ml) was added and the reaction was stirred overnight in an ice bath. The product (Hep-EDA) was dried under vacuum. Methacrylated Sodium alginate (Alg-MA) (0.25 g) was slowly dissolved in 0.1M MES buffer (pH 5.6, 12.5 mL). N-ethyl-N'(3-dimethylaminopropyl) carbodiimide hydrochloric acid (EDC) (0.22 g) was added to Alg-MA solution followed by N-hydroxysuccinimide (NETS) (0.13 g). The reaction was allowed to stir at room temperature for 30 minutes. The dried Hep-EDA was dissolved in 10 ml of DI water and added to alginate solution and allowed to stir at room temperature for 24 hours. The Alg-MA-β-CD-Hep solution was purified via dialysis (MWCO=6-8 kDa) against deionized water for three-five days, and lyophilized to yield a dry product. Alg-MA-β-CD-Hep (0.25 g) was slowly dissolved in 0.1M MES buffer (pH 5.6, 12.5 mL). N-ethyl-N'(3-dimethylaminopropyl) carbodiimide hydrochloric acid (EDC) (0.22 g) was added to Alg-MA-β-CD-Hep solution followed by N-hydroxysuccinimide (NHS) (0.13 g). After mixing for 30 minutes at room temperature, RGD (25 mg) was added an mixed vigorously at room temperature for one day. The Alg-MA-β-CD-RGD solution was purified via dialysis (MWCO=6-8 kDa) against deionized water for three-five days, and lyophilized to yield a dry product.

Alg-MA-β-CD-Hep-RGD Synthesis (Option B) [Hep then β-CD the RGD]

Heparin sodium salt (Hep) (0.25 g) was slowly dissolved in 0.1M MES buffer (pH 5.6, 12.5 mL). N-ethyl-N'(3-dimethylaminopropyl) carbodiimide hydrochloric acid (EDC) (0.042 g) was added to the Hep solution followed by N-hydroxysuccinimide (NHS) (0.07 g). The reaction was allowed to stir at room temperature for 24 hours. A 20 molar excess of ethylenediamine (EDA) (1.11 ml) was added and the reaction was stirred overnight in an ice bath. The product (Hep-EDA) was dried under vacuum. Methacrylated Sodium alginate (Alg-MA) (0.25 g) was slowly dissolved in 27.7 ml of DI water. N-ethyl-N'(3-dimethylaminopropyl) carbodiimide hydrochloric acid (EDC) (0.22 g) was added to Alg-MA solution followed by N-hydroxysuccinimide (NETS) (0.13 g). The reaction was allowed to stir at room temperature for 24 hours. The dried Hep-EDA was dissolved in 10 ml of DI water and added to alginate solution and allowed to stir at room temperature for 24 hours. The Alg-MA-Hep solution was purified via dialysis (MWCO=6-8 kDa) against deionized water for three-five days, and lyophilized to yield a dry product. Alg-MA-Hep (0.25 g) was dissolved in 0.1M MES buffer (pH 5.6, 25 mL), to which EDC (0.33 g) and NETS (0.2 g) were added. β-CD-EDA (0.375 g) was added under vigorous mixing at room temperature for one day. The Alg-MA-β-CD-Hep solution was purified via dialysis (MWCO=6-8 kDa) against deionized water for three-five days, and lyophilized to yield a dry product. Alg-MA-β-CD (0.25 g) was slowly dissolved in 0.1M MES buffer (pH 5.6, 12.5 mL). N-ethyl-N'(3-dimethylaminopropyl) carbodiimide hydrochloric acid (EDC) (0.22 g) was added to Alg-MA-β-CD solution followed by N-hydroxysuccinimide (NETS) (0.13 g). After mixing for 30 minutes at room temperature, RGD (25 mg) was added and mixed vigorously at room temperature for one day. The Alg-MA-β-CD-RGD solution was purified via dialysis (MWCO=6-8 kDa) against deionized water for three-five days, and lyophilized to yield a dry product.

Proton Nuclear Magnetic Resonance ($^1$H-NMR) Spectroscopy

To verify acrylate and β-CD functional group conjugations onto the alginate backbone, non-modified alginate, Alg-MA, Alg-β-CD, and Alg-MA-β-CD were each dissolved $D_2O$ to create a 1% (w/v) solution. $^1$H-NMR was performed on a Bruker AVANCE III 500 MHz high-field NMR Spectrometer, for 64 scans at 20 Hz. The methacrylation was verified by the appearance of methacrylate (6.24, 5.78 ppm) and alginate methyl peaks (1.96 ppm). To qualitatively verify the successful synthesis of Alg-β-CD and Alg-MA-β-CD, lyophilized polymer was dissolved in $D_2O$. Protons associated with β-CD functional group show peaks between 1-3 ppm.

Rheological Characterization and Gelation Kinetics

An AR2000 stress-controlled rheometer (TA instruments) was used for the following experiments. A 20-mm diameter 1° 59'6" steel cone geometry with a gap height of 57 μm were used. Non-modified alginate, Alg-MA, Alg-β-CD, and Alg-MA-β-CD polymer solutions (4%, w/v) were prepared in PBS with photo-initiators added at the following final concentrations: 1 mM Eosin Y (photo-sensitizer), 125 mM triethanolamine (photo-initiator), 20 mM 1-vinyl-2-pyrrolidinone (catalyst). Solutions were equilibrated in complete darkness at room temperature for 48 hours before testing. Viscosity tests were performed on each test solution at increasing shear rates and at room temperature (n=3). Oscillatory experiments were performed on each test group at room temperature (n=5). For time sweep experiments, a 1% radial strain was applied at a frequency of 10 Hz. Strain sweeps were performed at 10 Hz, and frequency sweeps were performed at 0.5% radial strain.

Effect of Thermo-Responsive Guest:Host Chemistry

Oscillatory temperature sweeps were performed on alginate, Alg-β-CD, and Alg-MA-β-CD solutions (4%, w/v) blended with Pluronic® F-108 (1:1 weight ratio). The temperature was increased from 25° C. to 37° C. at a frequency of 1 Hz and 1% radial strain. The average of the three trials was reported.

Effect of Visible Light Crosslinking

Oscillatory time sweeps were performed on Alg-MA and Alg-MA-β-CD solutions (4%, w/v), prepared in PBS with photo-initiators. The test was performed for 10 minutes at 37° C., a frequency of 1 Hz, and 1% radial strain. One minute after temperature equilibration, the polymer solution was exposed to visible green light (510 nm) via a custom light emitting diode (LED) ring placed around the gap. The average of the three trials was reported.

Sequential Tri-Crosslinking of Alg-MA-β-CD Hydrogels

To investigate the effect of chemical modification and various stimuli on the alginate materials, unmodified and modified alginate groups were exposed to heat, green light, and $CaCl_2$ in a sequential fashion. The polymer solutions (2%, w/v) were prepared as previously described with photo-initiators in PBS, and included Alg, Alg-MA, Alg-MA-β-CD with and without a 1:1 weight ratio of Pluronic® F-127. Three oscillatory temperature and time sweeps were performed on each test group. The temperature increased from 25° C. to 37° C., while shearing at 1% radial strain at 1 Hz. One minute after temperature equilibration, the polymer solution was exposed to visible green light via a custom LED ring. After 10 minutes of light exposure, the LEDs were removed and 0.1M $CaCl_2$ (100 μL) was carefully added to the solution. The average of the three trials was reported.

Effect of Pluronic® Selection and Polymer Concentration

To investigate the effect of using two different Pluronic® copolymers, F-108 (PEG-b-PPG-b-PEG), and F-127 (PEO-b-PPG-b-PEO), and two different Alg-MA-β-CD polymer solution concentrations, various polymer blends were prepared. Two and 4% (w/v) Alg-MA-β-CD solutions, with 1:1 weight ratios of Pluronic® copolymer, were prepared and analyzed for tri-crosslinking abilities. The average of the three trials was reported.

Human Mesenchymal Stem Cell (hMSC) Encapsulation hMSC Culture

Human MSCs were seeded in T75 tissue culture flasks at a density of ~0.3×10$^6$ cells per flask, in 10 mL of standard MSC growth media (alpha MEM supplemented with 10%

FBS, 100 U mL$^{-1}$ penicillin, 100 mg mL$^{-1}$ streptomycin), and cultured at 37° C. and 5% CO$_2$ until 80% confluent. hMSCs were expanded to create a stock solution of 10$^5$ cells/mL.

hMSC Encapsulation and Needle Ejection

Alg-MA-β-CD solutions (2%, w/v), with and without 1:1 weight ratio addition of Pluronic® F-127, were prepared under red light in MSC standard growth medium. The stock cell solution (200 2×10$^5$ hMSCs) was carefully added to the polymer solutions (Alg-MA-B-CD), and shear-thinning hydrogels (Alg-MA-β-CD:Pluronic® F-127, 1:1 weight ratio), and centrifuged for one minute at 1000 rpm to remove air bubbles; polymer solutions (Alg-MA-β-CD) and shear-thinning hydrogels (Alg-MA-β-CD:Pluronic® F-127, 1:1 weight ratio) encapsulating hMSCs were ejected from a syringe through an 18-G needle into a 35-mm tissue culture dish to form 3-mm thick 3D hydrogel samples, exposed to green light for 3 minutes, and then covered with 1 mL of MSC standard growth medium.

hMSC Characterization

Viability assays were performed at the 36-hour time point; a Live/Dead Viability/Cytoxicity Kit (Molecular Probes) with excitation/emission levels for green (494 nm/517 nm) and red (528 nm/617 nm) was used to qualitatively determine hMSC viability after mixing, ejection, and 36-hour culture at 37° C., 5% CO$_2$. Under reduced lighting, one vial of ethidium homodimer-1 was added to one vial of calcein AM. Growth medium was removed from the petri dishes and 200 μL of the Live/Dead solution was added. Hydrogels stain were incubated with Live/Dead stain for 30 minutes. A fluorescence microscope (Nikon Eclipse E800) was used to image the Live/Dead fluorescent stain under 100× magnification. Images were collected using Metamorph (Molecular Devices) software.

Example 1: Synthesis and Characterization of Alg-MA-β-CD $^1$H-NMR spectral analysis confirmed the successful methacrylation of sodium alginate, as well as the conjugation of β-CD functional groups onto alginate and Alg-MA, respectively, in aqueous solution-based chemical reactions. The acrylate groups on Alg-MA and Alg-MA-β-CD were identified as peaks at 6.1 ppm and 5.7 ppm (FIG. 1B, 'a') as well as 1.9 ppm (FIG. 1B 'b' peak). The addition of the β-CD was verified and identified by the peak at approximately 1 ppm (FIG. 1B 'c' peak). It is important to note that β-CD conjugation occurred without losing the methacrylation peaks (FIG. 1B 'a' and 'b' peaks); however, it appears qualitatively that the peaks associated with acrylate groups decrease in area after β-CD conjugation.

Example 2: Rheological Characterization

Viscosity data collected on polymer solutions demonstrated a shear-thinning property at room temperature (25° C.), for modified and non-modified alginates, indicative of free-flowing polymer chains in solution with characteristic material properties (controls versus experimental samples, FIG. 2A). During the duration of the 10-minute oscillatory time sweeps of the different polymer solutions, all the polymer solutions remained relatively stable (FIG. 2B). Due to the possibility of chain degradation during the methacrylation and β-CD complexation, it was expected that the non-modified alginate materials could exhibit the highest shear storage moduli (G') values, with G' decreasing in correlation with the polymer modifications; however, it was noted that the Alg-MA-β-CD materials recovered part of their stiffness and displayed a greater dependence on frequency compared to the other materials (FIG. 2B-D).

Example 3: Alg-MA-β-CD Hydrogel Gelation Kinetics

Figure 3B:
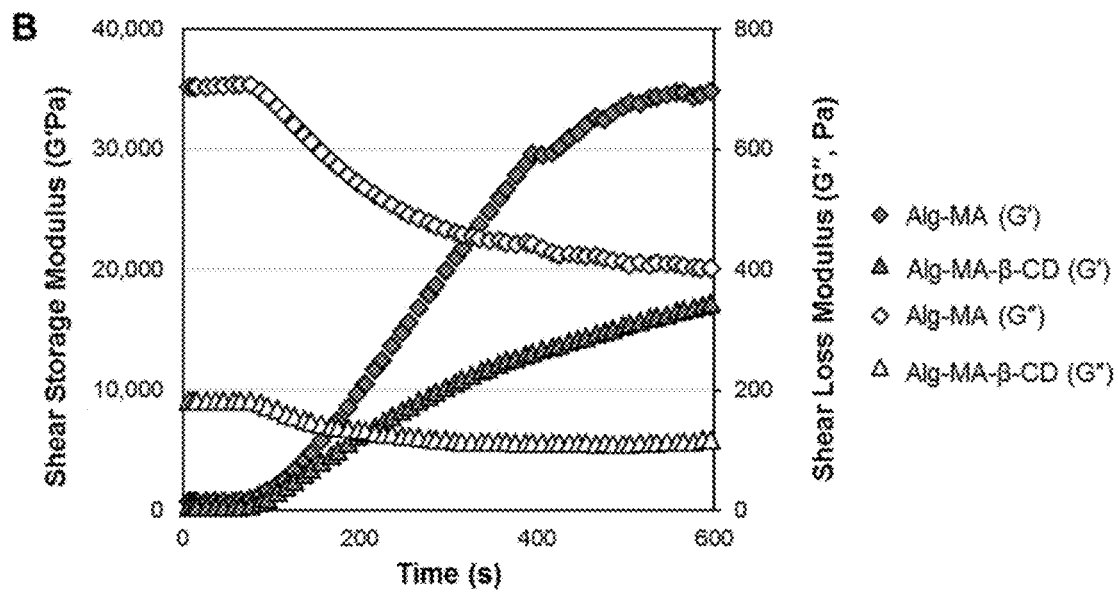

The effects of thermo-responsive guest:host chemistry, and visible light crosslinking, were determined on control (Alg) and experimental alginate materials (Alg-MA, CD), shown in FIGS. 3A-3B. The addition of a Pluronic® copolymer, F-108, yielded a variability in shear moduli correlating with increasing temperature. The presence of the F-108 was evident by the physical gelation upon heating of the control solution; heat may also increase dehydration, indirectly causing an increase in moduli (FIG. 3A). The Alg-β-CD and F-108 blend did not indicate complete gelation; however, the moduli were approaching a cross-over point. The Alg-MA-β-CD data indicated the formation of a supramolecular hydrogel, shown by the G'>G" relationship, and the increase in moduli with increasing temperature (FIG. 3A).

Upon exposure to visible green light for 10 minutes, G' increased to nearly 35 kPa, and 18 kPa, for Alg-MA and Alg-MA-β-CD hydrogels, respectively (FIG. 3B). Both materials were responsive to increasing heat and exposure to green light, with green light crosslinking showing the largest increase in G'. The Alg-MA material exhibited the longest gelation time (~350 s) compared to the Alg-MA-β-CD material (~180 s); while the Alg-MA material took longer to crosslink, the final moduli were nearly twice the values for Alg-MA-β-CD. The lower moduli for the Alg-MA-β-CD materials may be explained by acrylate and β-CD interactions, as indicated by the increased viscosity after subsequent methacrylation and β-CD conjugation.

Figure 4A:
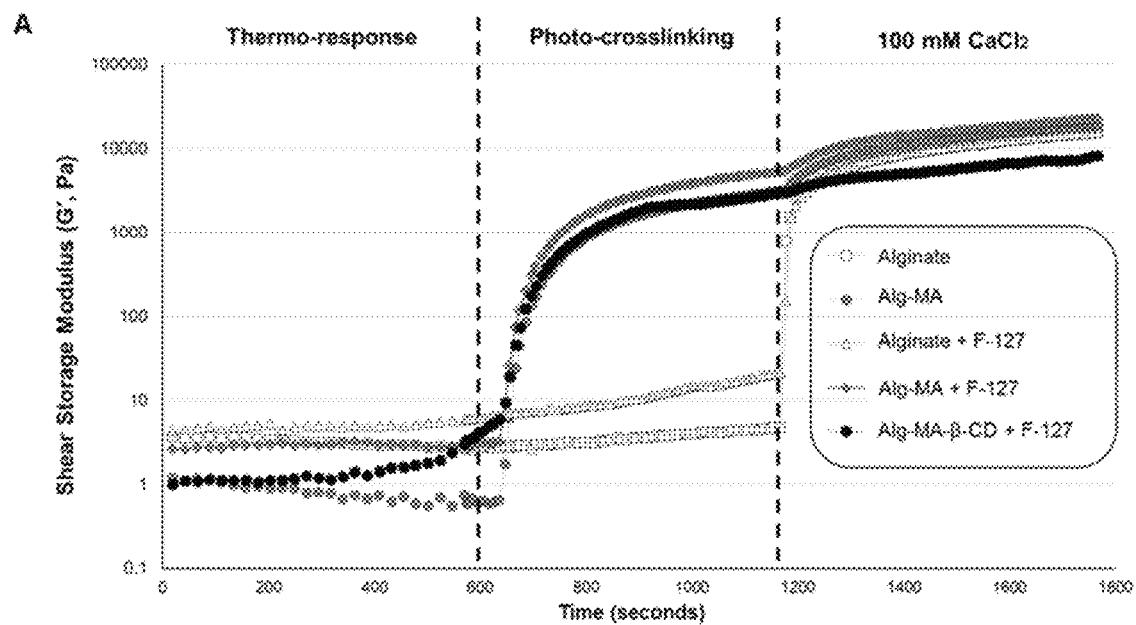
FIGS. 4A-4B are graphs showing gelation kinetics for 2% (w/v) alginate control (Alg), and chemically modified alginate (Alg-MA, Alg-MA-β-CD) hydrogels.
Figure 4B:
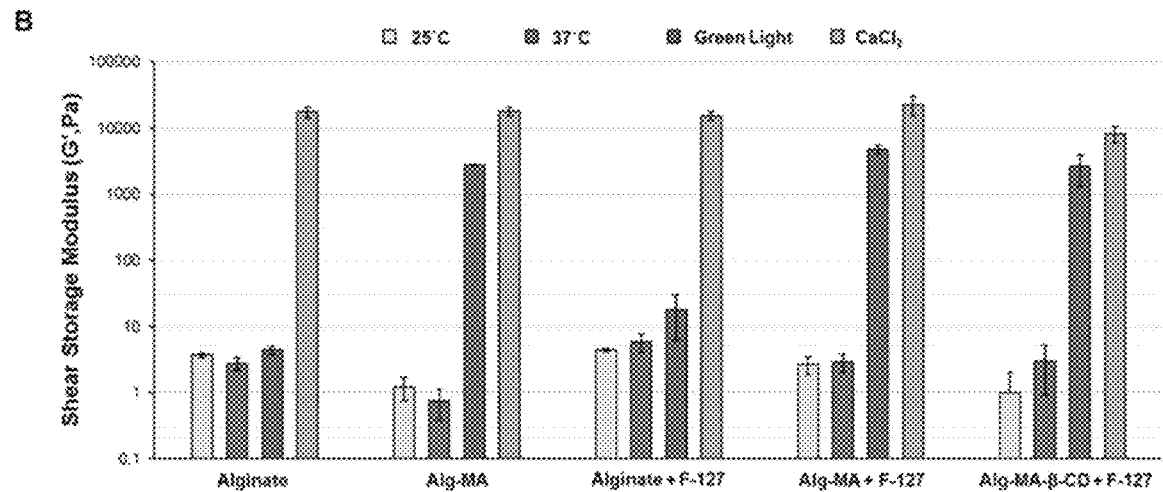

The sequential tri-crosslinking of chemically-modified alginate materials, to form a tri-network hydrogel, was successful, as shown by the increasing shear storage moduli (G') in FIGS. 4A-4B. All the polymer solutions studied study were 2% (w/v), and at this concentration, all three crosslinking techniques had an effect on the Alg-MA-β-CD material. There was a significant increase in G' for the alginate group, after exposure to green light, but this may have been caused by the dehydration of the alginate sample on the rheometer. The change in G' was minimal, increasing from 2.8 Pa to 4.4 Pa. For the non-modified alginate control solutions, there was a statistically significant increase in G' with the addition of calcium chloride which is expected (FIG. 4A, white squares); increasing from 4.4 Pa to 17.6 kPa. For the Alg-MA polymer solution, there was a statistically significant increase in G' after exposure to green light, and the subsequent addition of CaCl$_2$ (FIG. 4A, gray circles). It was expected that the Alg-MA group would exhibit a significantly large increase in G' after exposure to green light, given that covalent crosslinking occurs between acrylate groups with the photo-initiators in solution; the moduli increased from 0.75 Pa to 2.7 kPa. After ionic crosslinking, G' increased to 18.0 kPa. For the Alg:F-127 and Alg-MA:F-127 blends (FIG. 4A, white triangles and gray diamonds, respectively), there was not a significant increase in G' with increasing temperature, which was expected due to the absence of β-CD functional groups. However, as expected, there was a statistically significant increase in G' with the addition of CaCl$_2$ for the Alg:F-127 and Alg-MA:F-127 blends, with final G' values of 15.4 kPa and 22.8 kPa, respectively. For the Alg-MA-β-CD:F-127 hydrogel, there was not a significant increase in G' with increasing temperature (FIG. 4A, black circles). It was expected that the guest-host interactions would create a supramolecular hydrogel network prior to an increase in temperature, due to the interaction of β-CD functional groups and the PPG component of F-127. The storage moduli for Alg-MA-β-CD:F-127 hydrogels continued to increase significantly with exposure to green light (G'=2.6 kPa) and ionic crosslinking (G'=8.3 kPa). The quantitative G' values for the modified alginate hydrogels are shown in FIG. 4B.

While the above study verified external control of the hydrogel stiffness, selection of pre-curser molecules and polymer density played a significant role in varying hydrogel stiffness.

Figure 5A:
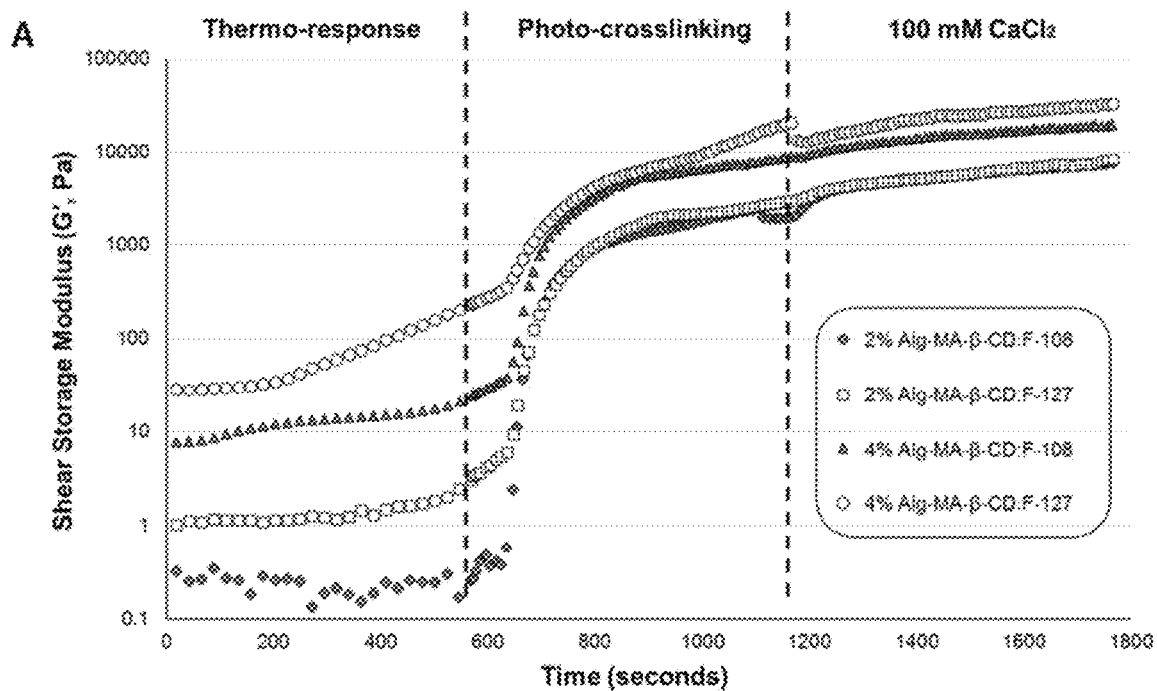
FIGS. 5A-5B are graphs showing gelation kinetics for 2% and 4% (w/v) blended with either Pluronic® F-108 or Pluronic® F-127.
Figure 5B:
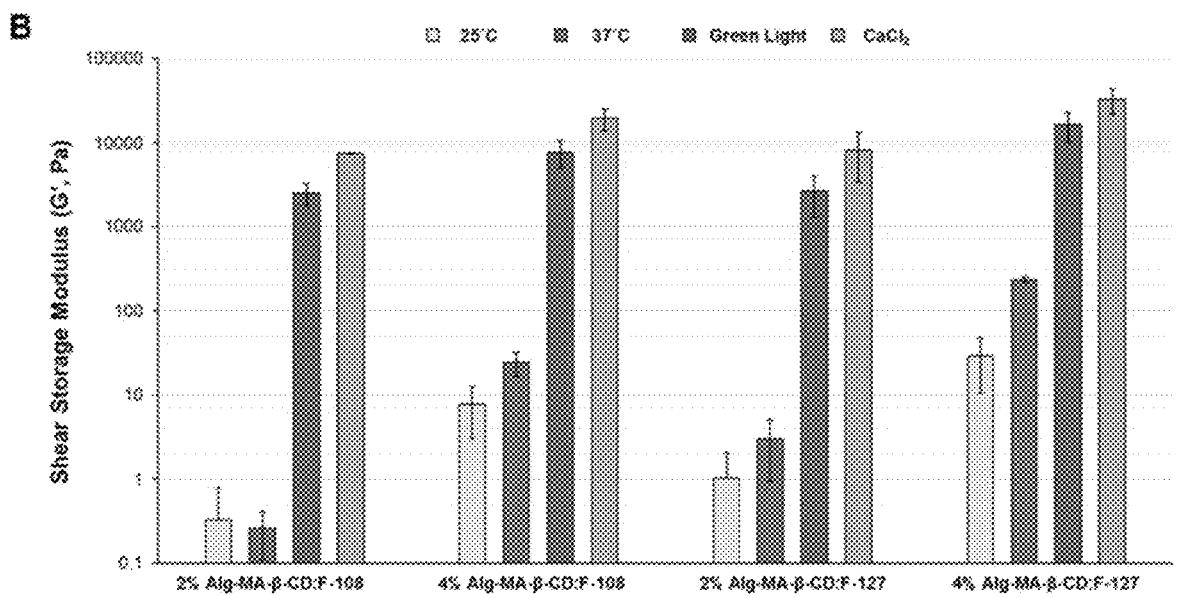

Both the polymer concentration and Pluronic® selection had an impact on G' of chemically modified alginate hydrogels. As shown in FIGS. 5A-5B, there was a large quantitative impact observed by increasing the polymer solution from 2 to 4% (w/v), and changing the Pluronic® component from Pluronic® F-108 (PEG-b-PPG-b-PEG) to Pluronic® F-127 (PEO-b-PPG-b-PEO). G' values, after the tri-crosslinking techniques were applied, for 2% (w/v) Alg-MA-β-CD:Pluronic® hydrogels, increased from 7.5 kPa to 8.3 kPa for F-108 and F-127 blends, respectively. Upon switching to a 4% (w/v) polymer concentration, G' values, after the tri-crosslinking techniques were applied, were 19.7 kPa and 32.7 kPa, respectively. The quantitative G' values for the Alg-MA-β-CD:Pluronic® hydrogels are shown in FIG. 5B. Indeed, the 4% tri-crosslinked Alg-MA-β-CD:F-127 hydrogels achieved the highest stiffness.

Figure 6:
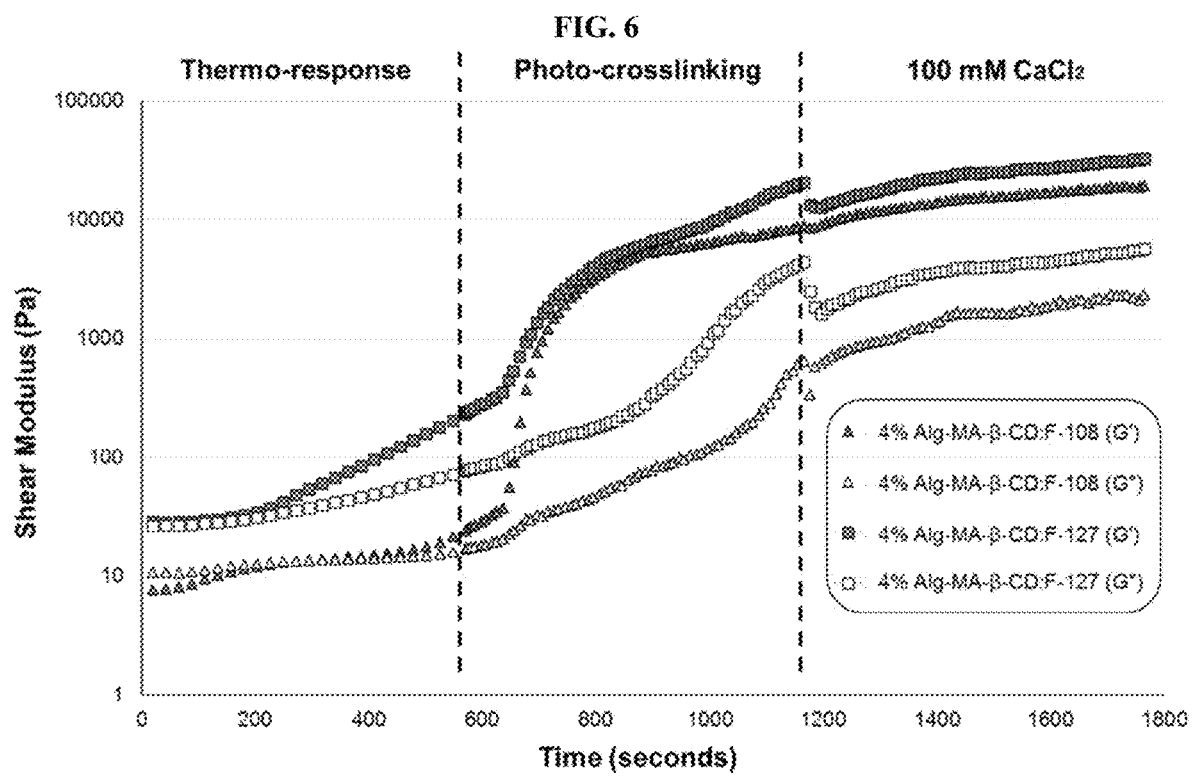
FIG. 6 is a graph showing gelation kinetics for 4% (w/v) Alg-MA-β-CD, blended with either Pluronic® F-108 or Pluronic® F-127. Shear storage (G') and loss (G") moduli were calculated after performing the following rheological methods: 1) Increasing temperature from 25° C. to 37° C., at 1% radial strain and 1 Hz, to examine the effects of β-CD conjugation, and Pluronic® addition (1:1 weight ratio); 2) exposure to green light, after 1 minute of equilibration at 37° C., for 10 minutes at 1% radial strain, 1 Hz, and 37° C., to examine the effect of covalent crosslinking on modified alginate materials; and 3) addition of 100 mM calcium chloride ($CaCl_2$) solution to examine the effects of ionic crosslinking on the modified alginate materials (after increasing temperature and covalent crosslinking).
Figure 7:
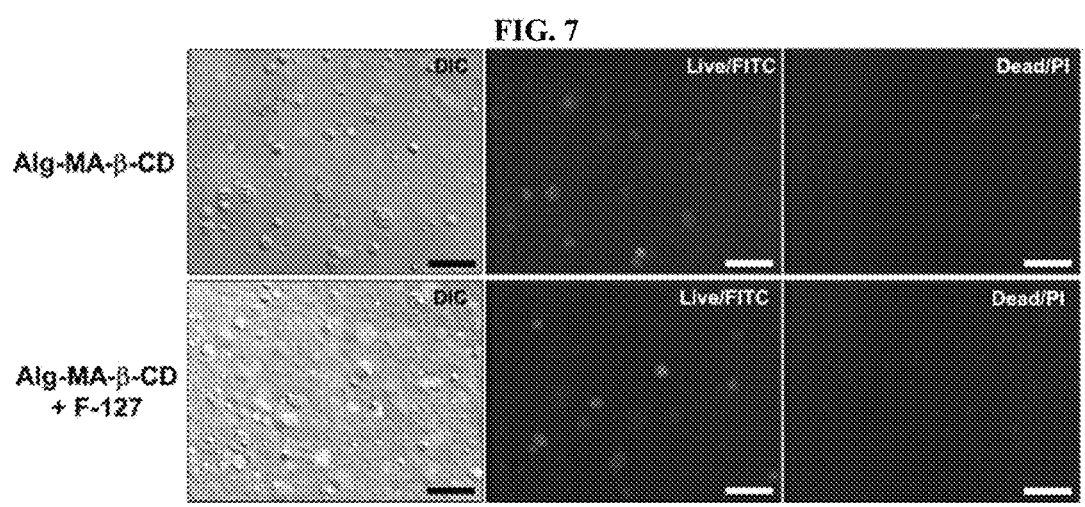
FIG. 7 is a set of images showing human MSCs thoroughly mixed and encapsulated within Alg-MA-β-CD solutions and Alg-MA-β-CD:Pluronic® F-127 hydrogels (1:1 weight ratios), and ejected through an 18-G syringe. A Live/Dead Viability/Cytoxicity Kit was used to qualitatively determine human MSC viability after mixing, ejection, and 36-hour culture within the 3-D hydrogels at 37° C., 5% $CO_2$. Fluorescent microscopy images were captured at 100× magnification; left=phase contrast image, middle=green indicates viable cells, right=red indicated dead cell. Scale bar=100 μm.

The effect of Pluronic® selection can be seen in the oscillatory temperature sweep, examining the G' and G" values for the chemically modified alginate materials, and display of supramolecular network behavior (FIG. 6). The hydrogels made with F-127 formed supramolecular complexes upon mixing, represented by the G'/G relationship. The hydrogels made with F-108 did not gel until after heat was applied. Even after a physical interaction and a supramolecular network is formed, the hydrogel is able to increase its stiffness via applied heat, visible light exposure, and the addition of calcium salt.

Example 4: Stem Cell Encapsulation and Viability

Human MSCs were mixed within a 2% (w/v) Alg-MA-β-CD solution, with and without a 1:1 ratio of F-127, and were successfully ejected through an 18-G needle while encapsulated within alginate hydrogels. Qualitatively, the polymer solution containing F-127 had more initial resistance when ejecting due to guest-host interactions between the β-CD functional group and F-127 hydrophobic PPO block. Both 2% solutions suspended cells throughout the hydrogels, and prevented cells from sinking to the bottom of the culture dish prior to crosslinking under green light. The results show that after 36 hours of incubation, numerous viable cells remain in the hydrogel. This outcome provides evidence that the hydrogel can support MSC activity.

Example 5: Synthesis and Characterization of Alg-MA-β-CD-RGD Hydrogels

Methacrylic anhydride was reacted with sodium alginate and β-CD was grafted onto Alg-MA using a multi-step process as described elsewhere herein. Alg-MA-β-CD-RGD was synthesized by adding arginylglycylaspartic acid (CRGDS) 1% (w/v) during the last step before dialysis, and the mixture was allowed to stir at room temperature for 24 hours. The solution was then frozen and lyophilized to obtain a dry polymer (Alg-MA-β-CD or Alg-MA-β-CD-RGD). To form the hydrogel, Pluronic® F127 was added to phosphate buffer solution (PBS) to create a 1:1 ratio with Alg-MA-β-CD. Rheological data (n=3) was collected using an AR2000 stress-controlled rheometer with a 20 mm 1° 59'6" steel cone geometry head. Stage one of testing consisted of a temperature sweep and was performed at 10 Hz and 1% stain with a heating rate of 0.5° C./min from 25 to 37° C. Stage two consisted of an oscillary time sweep and was performed at 10 Hz and 1% stain at 37° C. while exposed to LED green light. Stage three was conducted with the same parameters but with the addition of 0.1M $CaCl_2$ rather than green light. A 2% concentration of Alg-MA-β-CD-RGD solution with a 1:1 ratio of F127 was prepared under red light in growth medium. Human mesenchymal stem cells (hMSCs) were added to create a density of 3 million cells/ml. Polymer solutions (300 µL) were ejected from a syringe through an 18G needle into a petri dish and covered with 1 ml of cell media and exposed to visible green light for 5 minutes. A Live/Dead Viability/Cytotoxicity Kit (Molecular Probes) was used to test for viability after 36 hours.

Figure 8A:
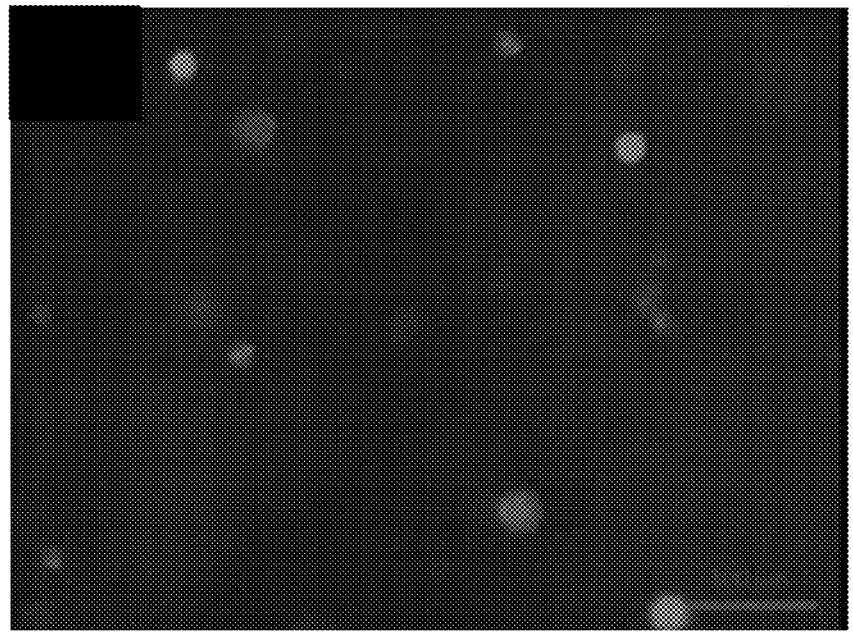
FIGS. 8A-8B are images of a live/dead assay performed on 2% Alg-MA-β-CD-RGD 1:1 Pluronic® F-127 hydrogel containing human MSCs after mixing, ejection, and 36-hour culture within the 3-D hydrogels at 37° C., 5% $CO_2$.
Figure 8B:
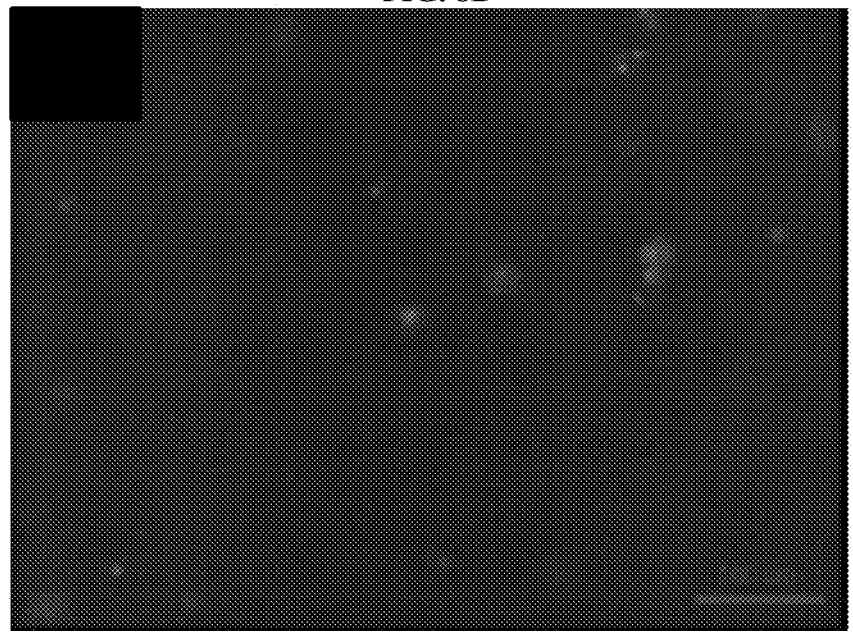

The storage modulus G' and loss modulus G" were plotted against time relating to the three different crosslinking techniques used (FIG. 4A). Fluorescent microscopy of 2% Alg-MA-β-CD-RGD 1:1 F127 hydrogel demonstrated that cells, specifically hMSCs, can survive ejection through a 18G needle and crosslink via temperature and green light (FIGS. 8A-8B).

Example 6: Sheer Thinning Property Comparisons

Figure 9:
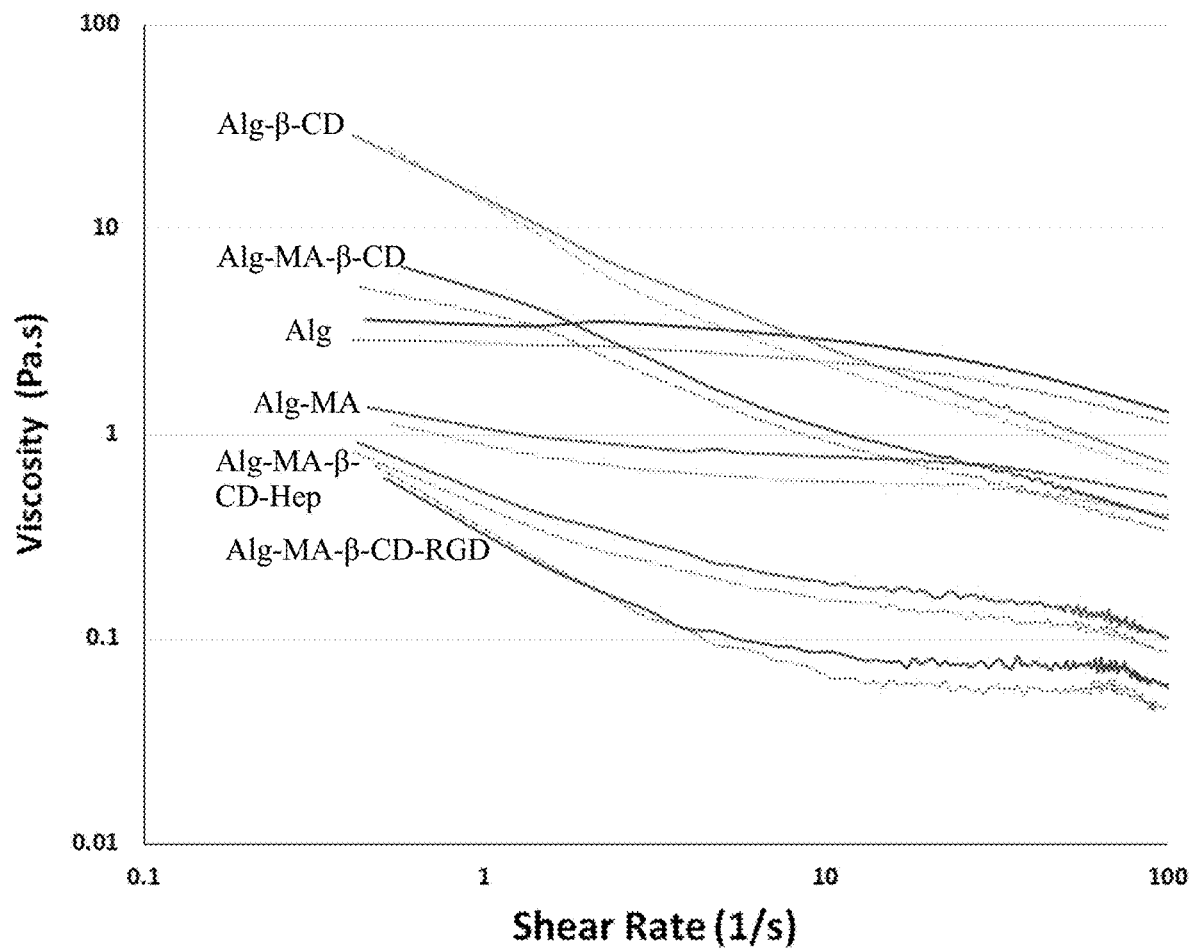
FIG. 9 is a graph plotting shear rate (1/s) versus viscosity (Pa.s.) for a variety of 2% (w/v) alginate-based polymer solutions at both 25° C. (solid lines) and 37° C. (dotted line). At a shear rate of 10 rotations/second, the unmodified alginate (Alg) demonstrated the highest viscosity, the cyclodextrin (Alg-β-CD), methacrylated (Alg-MA), and cyclodextrin and methacrylated (Alg-MA-β-CD) polymer solutions displayed lower viscosities and the biologically-modified materials, RGD modified (Alg-MA-β-CD-RGD) and heparin modified (Alg-MA-β-CD-Hep) polymer solutions displayed the lowest viscosities.

A variety of polymer solutions prepared according to the methods disclosed elsewhere herein were tested for shear thinning properties (FIG. 9). All of the alginate (control, Alg) and modified-alginate polymer solutions displayed shear-thinning behavior (i.e., viscosity decreased with increasing shear rate, and is controllable). All of the polymer solutions also displayed reduced viscosities at elevated temperatures. At a shear rate of 10 rotations/sec, the non-modified Alg solution displayed the highest viscosity. The cyclodextrin (Alg-B-CD), methacrylated (Alg-MA), and cyclodextrin and methacrylated (Alg-MA-B-CD) modified polymer solutions displayed lower viscosities compared to non-modified Alg. The biologically-modified materials, Alg-MA-B-CD-RGD and Alg-MA-CD-Hep displayed viscosities>1 order of magnitude less than other modified materials.

The disclosures of each and every patent, patent application, and publication cited herein are hereby incorporated herein by reference in their entirety. While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed is:

1. A hydrogel composition comprising:
   methacrylated alginate (Alg-MA);
   β-cyclodextrin (β-CD); and
   at least one additional component selected from the group consisting of heparin (hep) and arginylglycylaspartic acid (RGD);
   wherein the β-cyclodextrin (β-CD) and the at least one additional component are each covalently bound to the methacrylated alginate; and wherein the hydrogel composition has a viscosity of from about 0.05 Pa-s to about 0.5 Pa-s at a shear rate of 10 s$^{-1}$.

2. The hydrogel of claim 1, further comprising at least one crosslinking component selected from the group consisting of polypropylene glycol (PPG), polyethylene glycol (PEG), polyethylene oxide (PEO), PEG-b-PPG-b-PEG copolymers, PEO-b-PPG-b-PEO copolymers, agarose, amylase, amylpectin, cellulose, chitosan, collagen, fibrin, gelatin, glycogenhyaluronic acid, poly(acrylamide), poly(β-aminoester), poly(caprolactone), Matrigel, multi-arm polyethylene glycol, poly-hydroxyethyl acrylate, poly(hydroxyethyl methacrylate), poly(N-isopropylacrylamide), poly(glycolic acid), poly(lactic acid), poly(lactic acid-glycolic acid), oligo(poly(ethylene glycol)fumarate), poly(vinyl alcohol), poly(vinyl acid), 1-ethyl-3-[3-dimethylaminopropyl] carbodiimide hydrochloride (EDC), and N-hydroxysuccinimide (NHS).

3. The hydrogel of claim 2, wherein the methacrylated alginate and β-cyclodextrin forms a supramolecular complex with the at least one crosslinking component.

4. The hydrogel of claim 1, further comprising living cells.

5. The hydrogel of claim 4, wherein the living cells are encapsulated within the hydrogel composition.

6. The hydrogel of claim 4, wherein the living cells are eukaryotic cells.

7. The hydrogel of claim 4, wherein the living cells are progenitor cells.

8. The hydrogel of claim 7, wherein the living cells are human mesenchymal stem cells.

9. The hydrogel of claim 1, further comprising at least one pharmaceutically active compound.

10. The hydrogel of claim 9, wherein the at least one pharmaceutically active compound is encapsulated within the hydrogel composition.

11. The hydrogel of claim 9, wherein the at least one pharmaceutically active compound is non-covalently bound to the hydrogel composition through a guest-host interaction with the β-cyclodextrin moiety.

12. The hydrogel of claim 1, further comprising at least one biological factor.

13. The hydrogel of claim 12, wherein the at least one biological factor modifies one or more cellular functions selected from the group consisting of cell growth, cell viability, cell adhesion, tissue adhesion, and progenitor cell differentiation.

14. The hydrogel of claim 12, wherein the at least one biological factor is a heparin or RGD binding protein.

15. The hydrogel of claim 12, wherein the at least one biological factor is selected from the group consisting of epidermal growth factor (EGF), platelet derived growth factor (PDGF), basic fibroblast growth factor (bFGF), transforming growth factor-beta (TGF-β), and tissue inhibitors of metalloproteinases (TIMP).

16. The hydrogel of claim 12, wherein the at least one biological factor is non-covalently bound to the hydrogel composition through a guest-host interaction with the β-cyclodextrin moiety.

17. The hydrogel of claim 1, wherein the hydrogel composition is in the form of a microsphere composition.

18. The hydrogel of claim 17, wherein the microsphere composition comprises monodisperse microspheres.

19. The hydrogel of claim 17, wherein the microsphere composition comprises microspheres having a diameter of about 500 nm to about 80 μm.

20. A pharmaceutical composition comprising the hydrogel of claim 1.

21. The pharmaceutical composition of claim 20, further comprising at least one pharmaceutically acceptable carrier.

22. The pharmaceutical composition of claim 20, wherein the pharmaceutical composition is in a form selected from the group consisting of a cream, liquid, gel, spray, ointment, 3-D scaffold, powder, patch and graft.

23. A method of delivering viable living cells to a subject, the method comprising administering to the subject a hydrogel composition comprising alginate, β-cyclodextrin, living cells and at least one additional component selected from the group consisting of heparin and RGD wherein the at least one additional component is covalently bound to the alginate and wherein the alginate is methacrylated, and wherein the hydrogel composition has a viscosity of from about 0.05 Pa-s to about 0.5 Pa-s at a shear rate of 10 s$^{-1}$.

24. The method of claim 23, wherein the living cells are encapsulated within the hydrogel composition.

25. The method of claim 23, wherein the living cells are eukaryotic cells.

26. The method of claim 23, wherein the living cells are progenitor cells.

27. The method of claim 23, wherein the living cells are human mesenchymal stem cells.

28. The method of claim 23, wherein the method treats at least one disease or disorder in the subject selected from the group consisting of immune-mediated diseases, skeletal tissue injury, skeletal/cranial tissue injury, skeletal diseases, skin wounds, internal organ wounds, cancers, inflammatory diseases, infections, and chronic wounds.

29. A method of treating a wound in a subject in need thereof, the method comprising contacting the wound with a hydrogel composition comprising alginate, β-cyclodextrin modified alginate, living cells and at least one additional component selected from the group consisting of heparin and RGD wherein the at least one additional component is covalently bound to the alginate, wherein the alginate is methacrylated, and wherein the hydrogel composition has a viscosity of from about 0.05 Pa-s to about 0.5 Pa-s at a shear rate of 10 s$^{-1}$.

30. The method of claim 29, wherein the living cells are encapsulated within the hydrogel composition.

31. The method of claim 29, wherein the living cells are eukaryotic cells.

32. The method of claim 29, wherein the living cells are progenitor cells.

33. The method of claim 29, wherein the living cells are human mesenchymal stem cells.

34. The method of claim 29, wherein the hydrogel composition is in the form of cream, liquid, gel, spray, ointment, 3-D scaffold, powder, patch or graft.

35. The method of claim 29, wherein the hydrogel composition is disposed on the surface of a bandage, patch, secondary hydrogel scaffold or graft.

* * * * *